(12) United States Patent
Hao et al.

(10) Patent No.: US 9,877,795 B2
(45) Date of Patent: Jan. 30, 2018

(54) OPTICAL TARGETING AND VISUALIZATION OF TRAJECTORIES

(71) Applicant: iMIRGE Medical INC., London (CA)

(72) Inventors: Wang Hao, London (CA); Neil Duggal, London (CA)

(73) Assignee: iMIRGE Medical INC, London (CA)

( * ) Notice: Subject to any disclaimer, the term of this patent is extended or adjusted under 35 U.S.C. 154(b) by 494 days.

(21) Appl. No.: 14/490,610

(22) Filed: Sep. 18, 2014

(65) Prior Publication Data

US 2015/0080740 A1 Mar. 19, 2015

Related U.S. Application Data

(60) Provisional application No. 61/879,620, filed on Sep. 18, 2013, provisional application No. 62/051,784, filed on Sep. 17, 2014.

(51) Int. Cl.
*A61B 5/05* (2006.01)
*A61B 90/11* (2016.01)
(Continued)

(52) U.S. Cl.
CPC ............ *A61B 90/11* (2016.02); *A61B 8/4416* (2013.01); *A61B 8/4438* (2013.01);
(Continued)

(58) Field of Classification Search
CPC ................ A61B 90/11; A61B 17/1703; A61B 2090/3954; A61B 2090/3966;
(Continued)

(56) References Cited

U.S. PATENT DOCUMENTS 7,281,849 B2 6/1991 Bernhard et al.
5,212,720 A 5/1993 Landi et al.
(Continued)

FOREIGN PATENT DOCUMENTS

| CN | 102813504 | 12/2012 |
| JP | 2003260064 A | 9/2003 |
| WO | WO2015039246 | 3/2015 |

OTHER PUBLICATIONS https://www.healthcare.siemens.com/angio/options-and-upgrades/clinical-software-applications/syngo-iguide Believed to have been published on or before Aug. 12, 2014.

*Primary Examiner* — Sanjay Cattungal
(74) *Attorney, Agent, or Firm* — David Meibos; Maywood IP Law

(57) ABSTRACT

Enhanced targeting systems and methods may be used to visualize trajectories for surgical instruments. Such a targeting system may have a fixture that can be secured at a predetermined location relative to a patient, a first light source attached to the fixture, and a second light source attached to the fixture. The first light source may project first light along a first plane, and the second light source may project second light along a second plane nonparallel to the first plane. At an intersection of the first and second planes, the first light and the second light may cooperate to produce a targeting line that indicates the desired trajectory. A controller may be connected to first and second sets of motors to orient the first and second light sources, respectively. The targeting line may be projected on a visualization aid that guides the surgical instrument along the trajectory.

18 Claims, 19 Drawing Sheets

(51) Int. Cl.
  *A61B 8/00* (2006.01)
  *A61B 17/00* (2006.01)
  *A61B 90/13* (2016.01)
  *A61B 90/00* (2016.01)
  *A61B 34/10* (2016.01)
  *A61B 17/17* (2006.01)

(52) U.S. Cl.
  CPC .......... *A61B 17/1703* (2013.01); *A61B 90/13* (2016.02); *A61B 90/361* (2016.02); *A61B 2017/00398* (2013.01); *A61B 2034/107* (2016.02); *A61B 2090/363* (2016.02); *A61B 2090/364* (2016.02); *A61B 2090/3916* (2016.02); *A61B 2090/3954* (2016.02); *A61B 2090/3966* (2016.02); *A61B 2090/3991* (2016.02)

(58) Field of Classification Search
  CPC ........ A61B 2034/107; A61B 2090/364; A61B 90/361; A61B 2090/3991; A61B 90/13; A61B 2090/363; A61B 2090/3916; A61B 2017/00398; A61B 8/4438; A61B 8/4416
  USPC .......................................... 600/424; 606/130
  See application file for complete search history.

(56) References Cited

U.S. PATENT DOCUMENTS

| | | |
|---|---|---|
| 5,230,623 A | 7/1993 | Guthrie et al. |
| 5,662,111 A | 9/1997 | Cosman |
| 8,265,731 B2 | 9/1997 | Masahide et al. |
| 5,782,842 A | 7/1998 | Kloess et al. |
| 5,807,387 A | 9/1998 | Druais |
| 6,178,340 B1 | 1/2001 | Svetliza |
| 7,603,163 B2 | 10/2009 | McNeirney et al. |
| 8,246,352 B2 | 8/2012 | Takebayashi |
| 8,271,069 B2 | 9/2012 | Jascob et al. |
| 8,332,012 B2 | 12/2012 | Kienzle, III |
| 8,412,308 B2 | 4/2013 | Goldback |
| 8,467,851 B2 | 6/2013 | Mire et al. |
| 8,467,852 B2 | 6/2013 | Csavoy |
| 8,473,026 B2 | 6/2013 | Ferre et al. |
| 2009/0274271 A1* | 11/2009 | Pfister ............... A61B 6/12 378/62 |
| 2014/0107473 A1* | 4/2014 | Dumoulin ........... A61B 17/17 600/424 |
| 2014/0276000 A1* | 9/2014 | Mullaney ........ A61B 19/5244 600/424 |

* cited by examiner

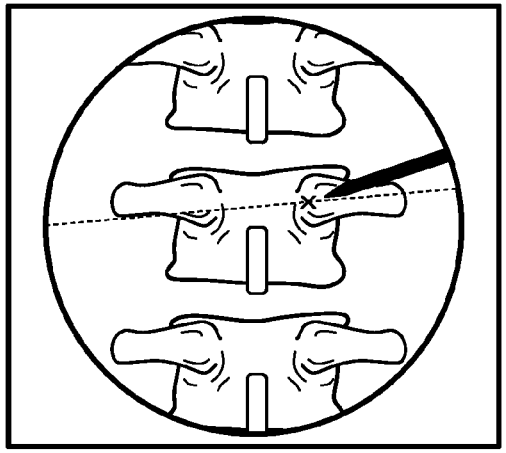 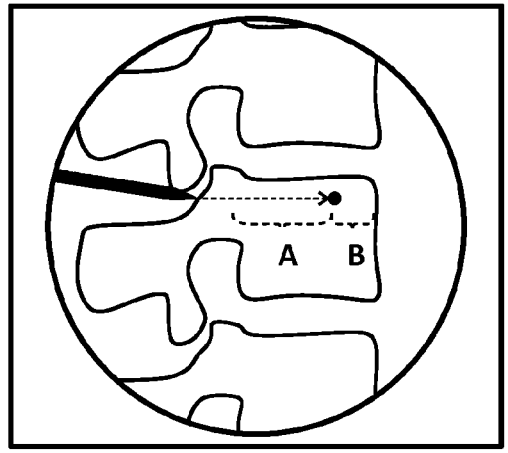
*Fig. 11A*   *Fig. 11B*
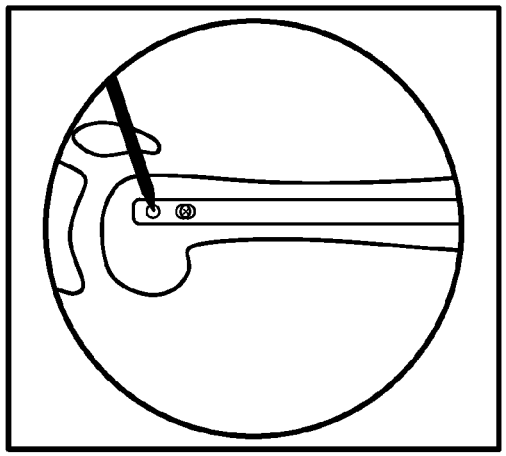 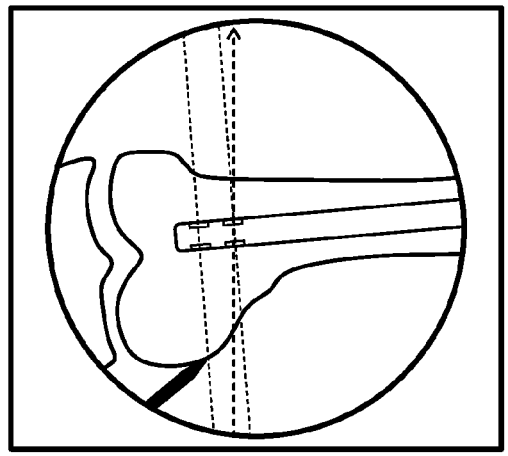
*Fig. 12A*   *Fig. 12B*

OPTICAL TARGETING AND VISUALIZATION OF TRAJECTORIES

CROSS-REFERENCE TO RELATED APPLICATIONS

The present application claims the benefit of U.S. Provisional Application Ser. No. 61/879,620, entitled OPTICAL TARGETING AND VISUALIZATION OF TRAJECTORIES, which was filed on Sep. 18, 2013. The present application also claims the benefit of U.S. Provisional Application Ser. No. 62/051,784, entitled OPTICAL TARGETING AND VISUALIZATION OF TRAJECTORIES, which was filed on Sep. 17, 2014. The foregoing are incorporated by reference as though set forth herein in their entirety.

TECHNICAL FIELD

The present invention relates to medical systems and methods. More specifically, the present invention relates to systems and methods for aligning medical instruments with anatomical targets.

BACKGROUND

Various imaging techniques, such as X-rays, fluoroscopy, ultrasound, computed tomography (CT), and magnetic resonance imaging (MRI) play an integral role in a wide variety of medical procedures. The term "image assisted" has been adopted to distinguish these procedures that are performed through the use of some type of imaging-based systems.

The incorporation of image guidance systems into various procedures allows a physician to correlate a desired location on a patient's anatomy to images taken pre-operatively or intra-operatively using various imaging modalities such as x-rays, ultrasounds, CT scans, or MRI's. The use of image guidance systems also imparts the ability to look through superficial layers of anatomy to visualize deeper targets of interest. Further, image guidance systems provide the guidance needed to access target areas of interest within the patient's anatomy through the use of pre-defined entry and/or target zones. Often, physicians rely heavily on imaging systems when a target cannot be directly visualized in order to avoid damage to surrounding anatomical structures and to minimize unnecessary tissue trauma.

There are at least two "spaces" used in image guidance systems. The first is the "image space," which is the imaging acquired prior to or during a procedure, such as an MRI scan of a specific anatomical area done before surgery. From cross-sectional imaging, a three-dimensional data set may be constructed using the first image space's coordinate system, usually expressed as a Cartesian system with an arbitrary origin and principle axis. The second space is the actual physical space surrounding the patient. This is often restricted to a specific anatomical part, such as the head, lower back, hip joint, etc., in order to improve local resolution and system performance. An image guidance system may include a mechanism for accurately measuring position within the patient's physical space, much like a tracking device. The tracking device may have its own coordinate system different from that of the "image space." In order to provide flexibility, there is often a "reference" that is held in a rigid relationship relative to the patient's anatomical area of interest. The reference serves as an arbitrary origin of the patient's physical space and all three-dimensional spatial measurements made can be expressed relative to this reference. The use of a reference allows for the movement of the image guidance system or for the manipulation of the target anatomical region without losing registration or affecting guidance accuracy.

After the two coordinate systems have been established, the image space may be correlated to the physical space through a process known as registration. Registration refers to the coordinate transformation of one space into another. This is usually a linear and rigid transformation in which only translation and rotation takes place (no scaling and no local deformation).

Once registration is completed, a probe or other device may be used to touch various anatomical structures on the subject (physical space), and the corresponding images of the same anatomical structures may be displayed (image space). The image guidance system may have the added advantage of multi-planar reconstruction, which allows the three-dimensional image dataset to be displayed in any arbitrary plane, further allowing users to view the surrounding structures through any arbitrary direction.

An image guidance system may include an information processing unit (e.g. a computer), which is used to load a patient's pre- or intra-operative images, as well as to run the software that will perform the registration between the image space and the physical space. The software program performs the registration between image space and physical space, and provides navigational information to the operator. This often includes the ability to perform multi-planar reconstructions and to perform targeting with specification of entry and target zones. More advanced functions include image fusion capabilities across imaging modalities such as fusing CT imaging data with MRI imaging data, as well as advanced image segmentation (e.g. extracting image information of a tumor or vessels and rendering three-dimensional models of these structures) to provide surgeons with live intraoperative guidance.

Another component of an image guidance system is the tracking device or reference that is used for spatial recognition. This device reads the coordinates of any point in three-dimensional space to allow accurate tracking of the physical space around the patient. An image guidance system also may include various probes to allow tracking of instruments, such as surgical instruments, endoscopic tools, biopsy needles, etc., during operation to provide flexibility with regards to navigational options. The probe may also act as the tracking device or reference.

Based on the aforementioned concepts, various advancements have been made that resulted in the inception of various image guidance systems. These systems differ on the exact detail of their execution regarding the various system components; however, many commonalties exist between the systems.

The most common system for spatial navigation is an optical system, such as that disclosed in U.S. Pat. No. 5,230,623. An optical system includes a stereo camera (i.e. two cameras mounted a known fixed distance apart) that cooperate to provide accurate three-dimensional localization. The method of tracking can be either passive or active. In passive tracking, the system emits infrared radiation (usually through a ring of infrared light emitting diodes, or LED's, mounted around each camera) and passive optical markers reflect the radiation back to the camera and allow the markers to be seen. The markers are usually small spheres of a pre-defined diameter coated in a reflective coating optimized for the wavelength of infrared radiation. With active tracking, the markers themselves consist of infrared LED's which emit infrared radiation that can be directly seen by the camera. Three or more markers arranged in a predefined geometry can be used to give total specification of a unique vector with 6 degrees of freedom (DOF)—3 in translation and 3 in rotation. By altering the predefined geometry of the markers, the system can recognize and simultaneously track various probes and tools, including the special "reference probe" that defines the arbitrary origin in the physical space. Optical systems typically come with proprietary software that performs image registration and provides navigational information to the end user.

Another system for spatial navigation is a magnetic system, such as the AxiEM™ navigation system marketed by Medtronic. A magnetic system employs a magnetic field generator to generate a uniform gradient field. A sensor is used to measure the strength and direction of the magnetic field, and based on this information, spatial localization is derived. Again, a reference point is fixed to the patient and various probes are available for flexible navigation.

Another system for surgical guidance is a stereotactic system. For cranial procedures, these systems rely upon the attachment of a rigid frame around a patient's head. Cross-sectional imaging (CT or MRI) may then be taken of the patient's head with the frame attached. The frame provides measurement of the physical space around the patient's head and correlates directly with the image space since the frame is captured on the scan. Registration of the image space and physical space occurs automatically once a common arbitrary coordinate system is chosen on the scan. Guidance is achieved mechanically, meaning that an external mechanism usually directs the surgeon's instrument down a machined groove or bore. The surgeon must rely solely on the trajectory calculations since no visual feedback is available in the absence of real-time imaging (e.g. intra-operative CT or MRI scanning).

Mechanical guidance can be expressed in various coordinate systems—Cartesian, polar, spherical, or mixed. The Leksell Stereotactic System® marketed by Eleckta is a common stereotactic system in use today, and it uses a mixed system. It expresses the target in Cartesian coordinates of x, y and z. The mechanical guide relies on the "arc" principle, whereby the arc is always centered over the target. This allows the surgeon to pick any ring or arc angle to find the most optimal placement of an entry site. Alternatively, an entry site could be predefined and the arc/ring angles could be calculated. Various size guides are available to accommodate various instrument diameters. Since the system cannot provide live image guidance, its role is more limited to procedures such as biopsies or placement of electrodes. A more specialized application of the Leksell frame is encountered in gamma knife therapy to help localize the radiation target. Numerous other stereotactic frames are currently available on the market that essentially embody various iterations of the same underlying principle.

Image navigation has proven to be extremely useful in improving accuracy of targeting, avoiding damage to surrounding critical structures, and improving patient outcomes. However, accurate targeting of deep anatomical structures is challenging across multiple disciplines. There is a need for an image guidance system which facilitates identification of ideal trajectories that are not directly visualizable.

Several clinical applications would stand to benefit from such improved targeting methods. One example is the insertion of external ventricular drains (EVD) or ventricular shunts (ventricular peritoneal, ventricular atrial, ventricular pleural, etc.). This procedure is performed to release/redirect cerebrospinal fluid (CSF) and to monitor intracranial pressure (ICP). The current standard of care involves a blind passage of the ventricular catheter from the skin surface to the deep ventricular system in the brain via crude external landmarks. Current image guided systems used in this procedure rely upon rigid fixation of the head and access to the operating room. In addition, the use of existing image guided systems may significantly lengthen the procedure time, making their use in the emergency setting unsuitable, especially when urgent control of ICP is needed.

Another clinical application that could benefit from improved targeting methods is the performance of biopsies and related procedures. Accurate targeting of soft tissue, bone, fluid, or anatomical spaces may be used to facilitate biopsy, device placement, and/or pharmacological agent delivery. A common cranial application is a stereotactic biopsy. Traditional methods have focused on frame-based stereotactic biopsy that relies upon the application of a frame secured to the skull with sharp pins that penetrate the outer table of the skull (e.g. four pins for the Leksell Stereotactic System® marketed by Eleckta). This procedure is painful for the awake patient and cumbersome to set up. Recent advancements in image guidance systems have allowed the development of "frameless stereotaxy." In this instance, the pre-procedural application of a frame followed by imaging of the patient with his/her head in the frame is avoided. However, the head still needs to be rigidly fixed with penetrating pins in a skull clamp, such as the Mayfield® clamp marketed by Integra LifeSciences. Because of the pain of fixating the skull and the immobilization experienced with the 3-pinned Mayfield® system, the patients are typically given a general anesthetic. With frameless stereotaxy, the targeting information is shifted entirely to the guidance system and the screen. The surgeon may unfortunately need to periodically look away from his or her hands and surgical instruments to view a screen that helps guide the trajectory.

Similar systems have been deployed to place electrodes or other implants. For instance, deep brain stimulator or RF ablation electrode insertion into cranial structures employs similar steps as a stereotactic biopsy. In this instance, the goal is to place an implant into a pre-defined area of the brain. Again, utilizing similar image-guided techniques, abnormal fluid or soft tissue collections including, but not limited to intracerebral abscesses, hematomas, or protein collections can be accurately targeted.

There are numerous potential applications of image-guided techniques in orthopedic procedures, ranging from placement of implants to placement of nails, plates and screws. For example, in hip replacement surgeries, accurate placement of the acetabular cap with specific angles of abduction/adduction and flexion/extension has been shown to be an important factor in preventing premature wear and recurrent hip dislocations. Similarly, knee, shoulder, ankle and small joint replacements rely upon precise cuts in the adjacent bones to ensure anatomical alignment of the implant. Another example is the placement of pedicle screws in spinal surgery, which rely upon a precise trajectory and angle of insertion to prevent neurological injury and screw misplacement. Another frequent orthopedic application involves the placement of intramedullary nails in long bone fractures. Intramedullary nails may conform to the shape of the intramedullary canal, sometimes making accurate targeting and alignment of distal locking screw holes difficult. Unfortunately, although many attempts have been made, no satisfactory system yet exists that can easily address this problem without significantly lengthening the operative time.

Unfortunately, all of these techniques, whether major or minor, involve access to an image guidance system, a fixation method, and an operating room. Access to such facilities and instruments may not be feasible if an emergency procedure is needed, where the delay in bringing the patient to the operating room and setting up existing image guidance systems would result in catastrophic outcome for the patient. The physician is often forced to resort to crude external anatomical landmarks for guidance. This trade-off between speed and accuracy means that patients who require emergency procedures are often not able to receive the benefits of image-guidance. Further, existing image guidance systems are, in many instances, expensive and cost-prohibitive in smaller medical facilities. This restricts access to image guidance technology to large, well-funded hospitals. Many hospitals and healthcare facilities are not equipped with traditional image guidance systems, depriving patients of the benefits of the accuracy and precision of image-guided procedures. This is particularly true in developing countries where cost is a major barrier to the adoption of image guidance technology. Additionally, routine radiology procedures such as biopsies are performed under the guidance of plain films, CT scans, ultrasound imaging, and magnetic resonance imaging. All of these imaging modalities require the practitioner to view an image on a screen, computer terminal, or the like, instead of watching the procedure in the physical space. These procedures are performed frequently and may expose radiologists and technicians to potentially harmful doses of radiation. When using existing image guidance systems, the users must take their eyes off the patient and focus on the information displayed on the screen ("eyes off target"). For these critical moments, the users do not have direct visual confirmation of their instrument(s). Instead they must rely on feel, muscle memory, and/or rapidly looking back and forth between the screen and the patient. Therefore, a need exists for an image guidance system that can use previous imaging studies to guide the physician as they target a structure hidden below the surface of the skin without the use of frames or pins while providing direct visualization within the working area of the targeting trajectory ("eyes on target").

SUMMARY OF THE INVENTION

The various systems and methods of the present invention have been developed in response to the present state of the art, and in particular, in response to the problems and needs in the art that have not yet been fully solved by currently available visualization systems. The systems and methods of the present invention may provide enhanced visualization systems that facilitate a variety of medical procedures.

To achieve the foregoing, and in accordance with the invention as embodied and broadly described herein, the present disclosure provides enhanced systems with associated methods to visualize desired trajectories. In one example of the disclosed technology, a targeting system incorporates a fixture and two or more light sources secured to the fixture at angles nonparallel to each other to facilitate the visualization of linear trajectories. Each light source may be a laser that projects light within a plane. The lasers can be tuned to the same frequency in the visible electromagnetic spectrum to produce the same colored light. In another embodiment, the lasers are tuned to different frequencies to produce different-colored light.

Each of the lasers may project a well-defined planar field of electromagnetic radiation along its principle axis. The principle axes of the lasers may be non-parallel to each other and non-coaxial with each other such that the light from the two or more lasers intersects to produce a targeting line in three-dimensional space. Adjustment of the orientation of the plane within which light is projected may be accomplished by adjusting the orientation (for example, roll, pitch, and/or yaw) of the corresponding light source. Adjustment of the orientation of either plane may result in repositioning of the targeting line. The targeting line may be coaxial with the trajectory for which visualization is desired. The targeting line may be visualized, for example, by projecting it on an instrument. Orientation of the instrument such that the targeting line is visible as a line on the instrument may indicate that the instrument is properly oriented along the trajectory.

The system may operate with either cross-sectional imaging or planar (projection) imaging modalities. One example of cross-sectional imaging involves trajectory planning performed using either source images or multi-planar reconstruction. One or more reference markers may be applied to the patient prior to image acquisition, and the reference marker(s) may be identified during trajectory planning. In an alternative embodiment, the system may include an image-capture device, such as a CCD camera, that may be used in conjunction with the movable light source mentioned previously, to capture 3D surface information of the patient. The planned trajectory may be plotted and used, in combination with either the reference marker location(s) or the 3D surface information, to determine the orientations of the light sources that are required to project the targeting line at the trajectory. These orientations may be conveyed to the targeting system and used to set the orientations of the light sources. The targeting system may then be activated to project the targeting line, thereby indicating the trajectory proximate the point at which the instrument is to enter the patient's anatomy.

One example of planar imaging involves attaching the targeting system directly to a medical imaging device (for example, the image intensifier of a fluoroscopy unit). With the medical imaging device, two images may be taken orthogonal to each other of the anatomical region of interest, with rotation been the only allowed motion for the imaging device between capture of the two images. The planned trajectory may be plotted using the two orthogonal image projections. The medical imaging device may be rotated to a predefined angle prior to calculation of the orientations of the light sources. The predefined angle may be established by the user to keep the medical imaging device from impeding the procedure, while enabling the targeting system to provide the necessary trajectory visualization. Then, the trajectory may be used to generate the appropriate orientations for the light sources, which may be conveyed to the targeting system and used to set the orientations of the light sources. The targeting system may then be activated to project the targeting line. The visualized trajectory may optionally be coaxial with the central axis of the medical imaging device.

In some embodiments, additional light sources (for example, a targeting system incorporating three or more lasers) can be used to provide depth information, allow visualization of two or more trajectories simultaneously, and/or provide flexibility in the orientation of the targeting system. Thus, if the space between one or more light sources and the trajectory to be visualized is occluded by an object or person, two of the remaining light sources may instead be used to project the targeting line.

The disclosed technology is versatile and has a wide range of applications, including but not limited to: targeting anatomical structures for procedures such as biopsies, ablation, injections, electrical stimulation, and the like, guiding and/or aligning placement of implants such as joint replacements, screws, rods, and the like, directing the angle of osteotomies, and guiding the placement of other instruments such as catheters, ultrasound probe, rigid endoscopes, etc. The disclosed technology may also be used to facilitate the performance of current image guidance systems as well as robot-assisted procedures. Further, the disclosed technology may be used to perform dental applications such as alignment and/or placement of implant posts, definition of root canal trajectories, location of dental fractures, and the like. Further, the disclosed technology may be used in a variety of industrial applications to improve the alignment of manual procedures such as drilling, welding, finishing procedures, etc.

These and other features and advantages of the present invention will become more fully apparent from the following description and appended claims, or may be learned by the practice of the invention as set forth hereinafter.

BRIEF DESCRIPTION OF THE DRAWINGS

Exemplary embodiments of the invention will become more fully apparent from the following description and appended claims, taken in conjunction with the accompanying drawings. Understanding that these drawings depict only exemplary embodiments and are, therefore, not to be considered limiting of the invention's scope, the exemplary embodiments of the invention will be described with additional specificity and detail through use of the accompanying drawings in which:

FIGS. 11A-11B are dorsal and lateral views, respectively, illustrating how orthogonal images can be used for trajectory planning and visualization with a targeting system for a spinal procedure using a planar imaging modality.

FIGS. 12A-12B are lateral and dorsal views, respectively, illustrating how orthogonal images can be used for trajectory planning and visualization with a laser targeting system for an orthopedic procedure using a planar imaging modality.

DETAILED DESCRIPTION

Exemplary embodiments of the invention will be best understood by reference to the drawings, wherein like parts are designated by like numerals throughout. It will be readily understood that the components of the invention, as generally described and illustrated in the Figures herein, could be arranged and designed in a wide variety of different configurations. Thus, the following more detailed description of the embodiments of the apparatus, system, and method, as represented in FIGS. 1 through 22B, is not intended to limit the scope of the invention, as claimed, but is merely representative exemplary of exemplary embodiments of the invention.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1:
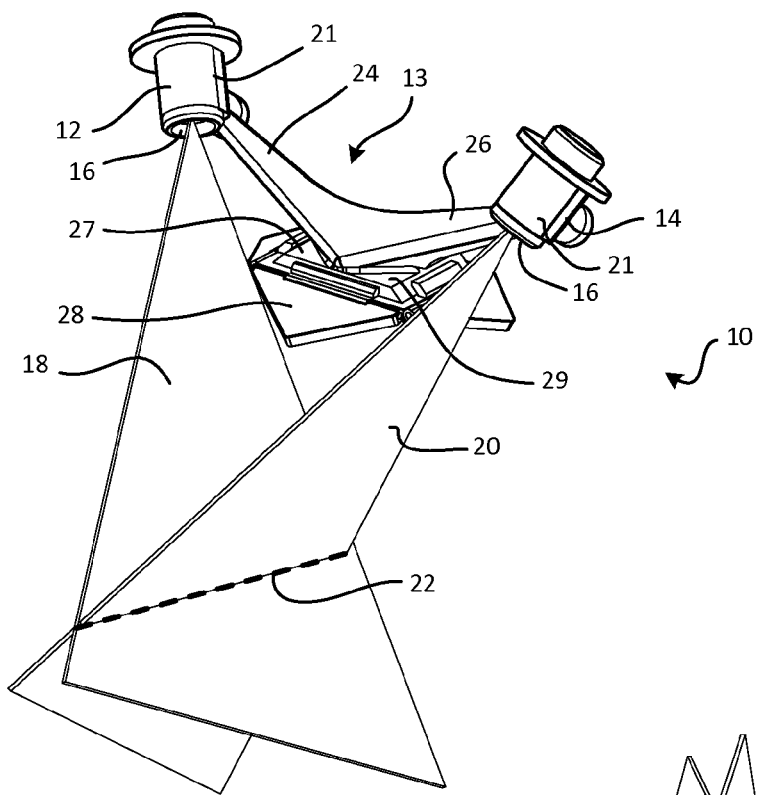
FIG. 1 is a perspective view illustrating a targeting system according to one embodiment, with two lasers that project light of different colors in intersecting planes to produce a targeting line at a desired trajectory, and a fixture in the form of a baseplate securable to a patient.

Referring to FIG. 1, a perspective view illustrates a targeting system, or system 10, according to one exemplary embodiment. The system 10 may also be referred to as an image guided laser targeting system, a targeting system, a laser guide, or a guided targeting system. As embodied in FIG. 1, the system 10 may be designed to be registered directly on a patient, as will be described subsequently. The system 10 may be well-adapted for cranial procedures such as the installation of external ventricular drains (EVD's) or the like, and may be used to project a targeting line along the trajectory a surgical instrument is to follow in order to properly perform the procedure.

As illustrated in FIG. 1, the system 10 includes a first light source in the form of a first laser 12 and a second light source in the form of a second laser 14. In various embodiments, a wide variety of light sources may be used, including but not limited to lasers, light-emitting diodes (LED's), incandescent lights, fluorescent lights, and the like. Coherent light sources and/or incoherent light sources may be used. Lasers may advantageously emit coherent light that can provide distinct and easily visible luminance, but in other embodiments, other types of light sources may be used.

The first laser 12 and the second laser 14 may each be designed to emit light along a plane. This may be accomplished, for example, by covering the emitting end of the laser with a slotted cover that permits light to exit only via the slot and/or aligning the laser light source with an optical lens that provides planar light output. Thus, the first laser 12 may emit first light along a first plane, and the second laser 14 may emit second light along a second plane, which may be nonparallel to the first plane.

The first laser 12 and the second laser 14 may be attached to a fixture that keeps the first laser 12 and the second laser 14 in fixed locations relative to each other and to the patient. In the system 10 of FIG. 1, the fixture may take the form of a base component 13 to which the first laser 12 and the second laser 14 are attached at a fixed relative distance from one another. The base component may be designed to register directly on an anatomical feature of the patient, such as the cranium.

In the system 10, the distance between the first laser 12 and the second laser 14 is fixed; however, in alternative embodiments, light sources can be movable relative to each other. The positions of the light sources may need to be accurately measured so that it can be accounted for in the calculations needed to accurately project a targeting line along the trajectory to be visualized. The distance between the first laser 12 and the second laser 14 may be optimized based on the proximity of the desired instrument trajectory to the system 10. The accuracy of the trajectory visualization may be improved by positioning the first laser 12 and the second laser 14 coplanar with a midpoint of the trajectory in an approximately equilateral triangular arrangement.

For example, in a neurosurgical setting, the base component 13 of the system 10 may be attached to a patient's forehead with the targeting area covering the convexity of the cranium. This arrangement may provide a most accurate targeting range of approximately 10 cm for the insertion of an EVD, a dimension corresponding to the distance between the first laser 12 and the second laser 14.

The first laser 12 and the second lasers 14 may each include a lens 16 that is at least partially encapsulated by a casing 21. The lens 16 and/or the casing 21 may be cylindrical. The lenses 16 may allow for the generation of first light 18 that originates from the first laser 12 and second light 20 that originates from the second laser 14. As shown, the first light 18 may be emitted along a first plane, and the second light may be emitted along a second plane nonparallel to the first plane.

The first laser 12 and the second laser 14 may be designed such that the first light 18 and the second light 20 are both predominantly composed of frequencies within the visible portion of the electromagnetic spectrum. The second light 20 may have a frequency different from that of the first light 18, and may thus have a color different from that of the first light 18. For example, the first light 18 may be red and the second light 20 may be green. In the rest of this specification, references to red and green lasers are to be interpreted as the first and second lasers, respectively, and are not an indication that red and green lasers are the only colors contemplated. In other examples, the second laser 14 may be movably mounted relative to the first laser 12 so that the position of the second laser 14 may be adjusted relative to that of the first laser 12. The lens 16 of the first laser 12 and/or the second laser 14 may be a Gaussian lens. Additionally or alternatively, the system 10 may include one or more additional lasers, which may have various lens types, emission frequencies, and/or other parameters.

The first light 18 and the second light 20 may each originate from a laser source within the corresponding one of the first laser 12 and the second laser 14. These laser sources may be, for example, a red laser diode (not shown) in the first laser 12 and a green laser diode (not shown) in the second laser 14. Laser diodes may provide compact size and favorable energy consumption, although other laser sources may be substituted for laser diodes. The red laser diode may emit electromagnetic radiation of approximately 650 nm. The green laser diode may emit electromagnetic radiation of approximately 530 nm. The first laser 12 and the second laser 14 may be positioned such that when the first light 18 and the second light 20 are emitted, they intersect to produce a targeting line 22, which in this example is perceived by the human eye as a yellow color due to the additive property of light. The additive color produced by adding the colors of the first laser 12 and the second laser 14 may add an additional element of distinctive visualization of the target trajectory. The additive color will vary depending on the colors of light emitted by the first laser 12 and the second laser 14. In other embodiments, one or more lasers that emit light of different wavelengths (for example, a laser that emits blue light with a wavelength of 450 nm) may be used in place of or in addition to the first laser 12 and/or the second laser 14.

The first laser 12 and the second laser 14 may be attached to the base component 13 in such a way that each has at least two degrees of rotational freedom about axes of rotation that are orthogonal to each other. For example, the first laser 12 and the second laser 14 may each be rotatable such that a relative geometrical relationship between the first laser 12 and the second laser 14 exists so that a third axis orthogonal to the first and second rotational axes remains fixed in rotation. The movement of the first laser 12 and the second laser 14 may be in the "yaw" and "roll" directions while having a fixed "pitch." In other embodiments, the first laser 12 and the second laser 14 may be fixed in rotation about the yaw direction or the roll direction, while rotation is possible about the other two directions. A translational degree of freedom may additionally or alternatively be incorporated if the distance between the lasers is adjustable.

To accurately calculate the "roll" and "yaw" of the first laser 12 and the second laser 14, the trajectory is transformed into the local coordinate system of each of the first laser 12 and the second laser 14 with the laser's center of rotation occupying the origin. The distance between the lasers is known. A plane originating from the center of the first laser 12 (the red laser) and coincident with the trajectory is the ideal path of the first light 18. The angle of the corresponding first plane with respect to the origin may be used to calculate the roll and yaw angles. The same procedure may be carried out for the second laser 14 (the green laser). Two planes coincident with the same line must therefore intersect at that and only that line (since two planes in 3-D space intersect to form a unique line). As such, the two unique sets of roll and yaw angles are sufficient to determine a unique targeting line that defines a trajectory in three-dimensional space based on the intersection of the first light 18 emitted by the first laser 12 with the second light 20 emitted by the second laser 14.

Figure 2:
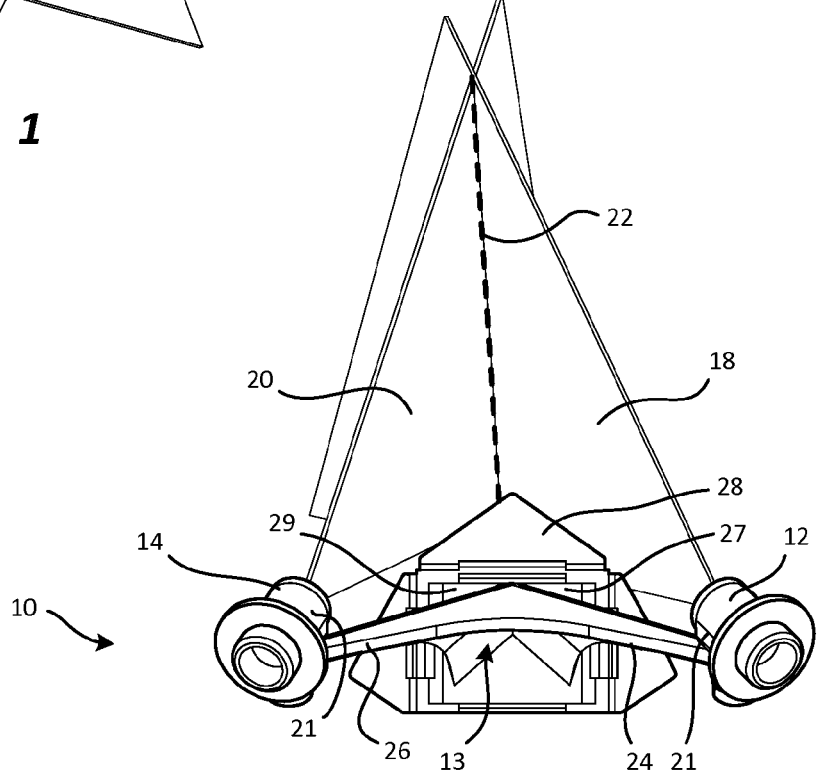
FIG. 2 is an alternative perspective view of the targeting system of FIG. 1 with the base component more easily visualized.

Referring to FIG. 2, an alternative perspective view illustrates the system 10 of FIG. 1 with the base component 13 more easily visualized. As shown, the base component 13 may have a first arm 24, a second arm 26, a base platform 27, and a baseplate 28. The first laser 12 may be attached to the first arm 24 of the base component 13, and the second laser 14 may be attached to the second arm 26 of the base component 13. The first arm 24 and the second arm 26 may intersect at or near a top surface 29 of the base platform 27. The base platform 27 may be attachable to the baseplate 28, which may be secured to a desired anatomical feature during use.

As embodied in FIG. 2, the baseplate 28 may be a general component that serves two main purposes. First, the baseplate 28 may provide a reference to allow accurate image registration. Second, the baseplate 28 may provide an interface to attach the system 10 to the patient. In alternative embodiments, baseplates may perform one or both of these functions with a configuration different from that illustrated in FIG. 2. Alterations or permutations in baseplate features may be made to adapt the system 10 to particular local anatomy or features, depending on the specific application the system 10 is to be used for.

The baseplate 28 may include a bottom surface (not shown in FIG. 2) opposite the top surface 29 that is shaped to interface with a top portion 31 (FIG. 3A) of the baseplate 28. The base platform 27 may include grooves, holes, channels, posts and/or other features that are shaped to engage complementary features on the top portion 31 of the baseplate 28 to secure the base platform 27 to the baseplate 28. The baseplate 28 may include a bottom portion 33 (FIG. 3B) opposite the top portion 31 that is shaped to interface with the desired anatomical part or feature for which trajectory visualization is performed. The bottom portion 33 may include an adhesive material or connection features, such as pins, screws, hook and loop fastener, or other protruding and/or recessed features that allow the system 10 to be substantially secured to the appropriate anatomical feature during the procedure.

Figure 3A:
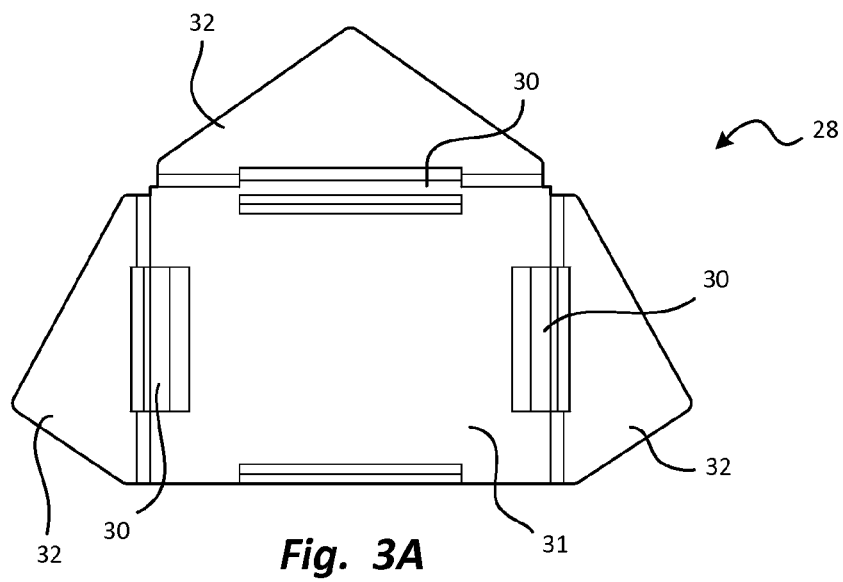
FIGS. 3A-3C are plan, front elevation, and perspective views, respectively, of the baseplate of the targeting system of FIG. 1, with hinged fins and embedded markers to aid visualization on imaging.
Figure 3B:
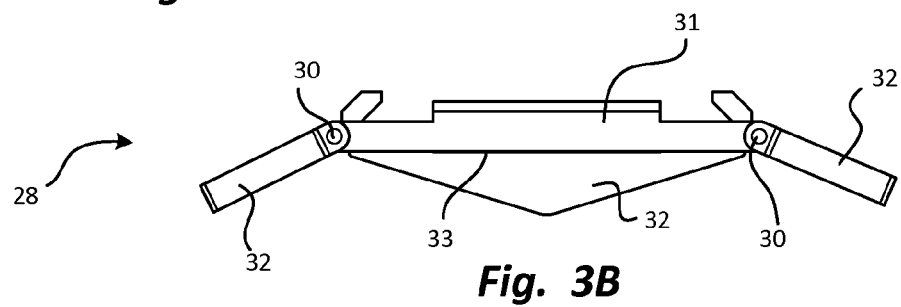
Figure 3C:
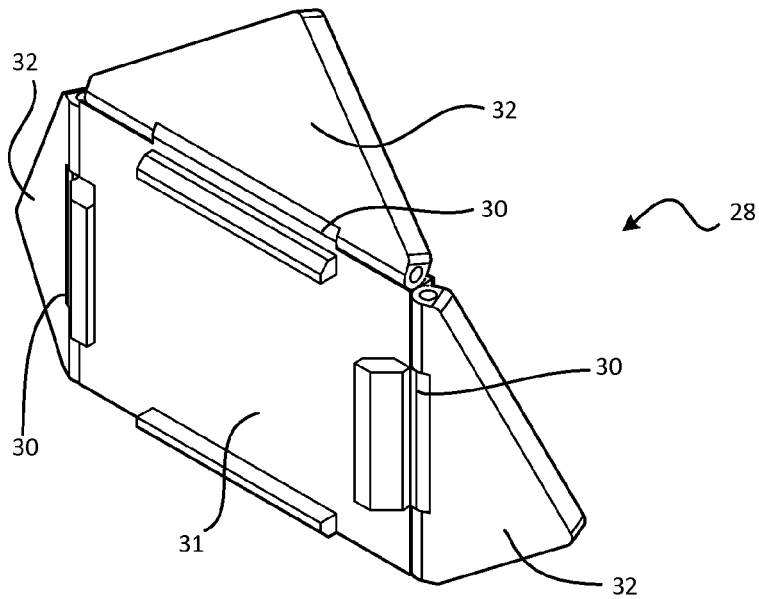

Referring to FIGS. 3A-3C, plan, front elevation, and perspective views, respectively, illustrate the baseplate 28 of the system 10 of FIG. 1. As shown, the baseplate 28 may be substantially flat, and may include one or more hinges 30, each of which defines an outside edge portion 32 in the shape of a fin. In alternative examples, the baseplate 28 may be curved or angled, in addition to or in place of the presence of hinges. Each hinge 30 may allow the corresponding one of the outside edge portions 32 to rotate about the hinge 30 to enable the baseplate 28 to conform to a complex surface topography. In the example illustrated in FIGS. 3A-3C, the baseplate 28 may include three hinges 30 such that three outside edge portions 32 may rotate about each associated hinge 30.

Figure 4A:
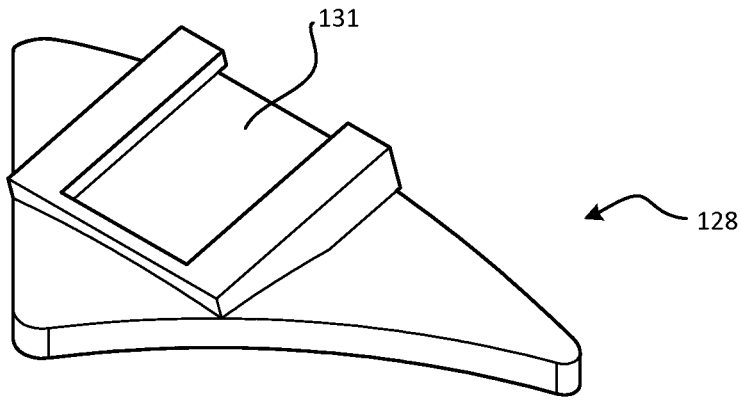
FIGS. 4A-4C are perspective, front elevation, and plan views, respectively, of a baseplate of a targeting system according to one alternative embodiment, with predefined curvature and no movable fins.
Figure 4B:
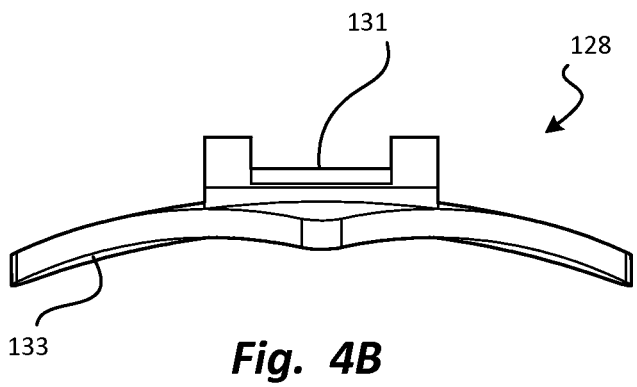
Figure 4C:
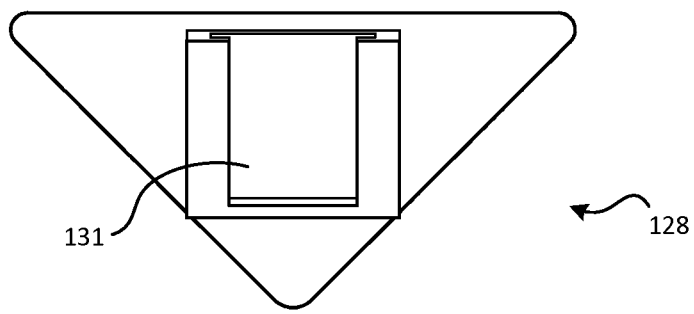

Referring to FIGS. 4A-4C, perspective, front elevation, and plan views, respectively, illustrate a baseplate 128 of a targeting system according to one alternative embodiment, with a predefined curvature and hinges or no movable fins. The baseplate 128 may have a bottom portion 133, which may have a predefined curvature to conform to a contoured anatomical surface. As shown in FIGS. 4A-4C, this curvature may be concave so that the baseplate 128 can conform to a convex surface such as a cranial surface. The baseplate 128 may also have a top portion 131 with a receptacle that mates with a corresponding feature (not shown) coupled to the first and second light sources (not shown).

Figure 5A:
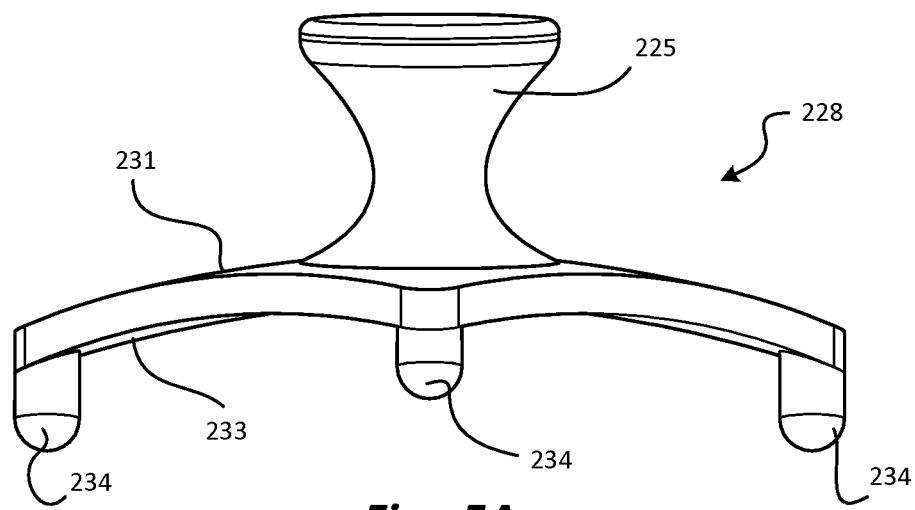
FIGS. 5A-5B are front elevation and perspective views, respectively, of a template for attaching a plurality of points or markers to the patient to serve as a reference for attachment of a targeting system such as that of FIG. 1 to the patient.
Figure 5B:
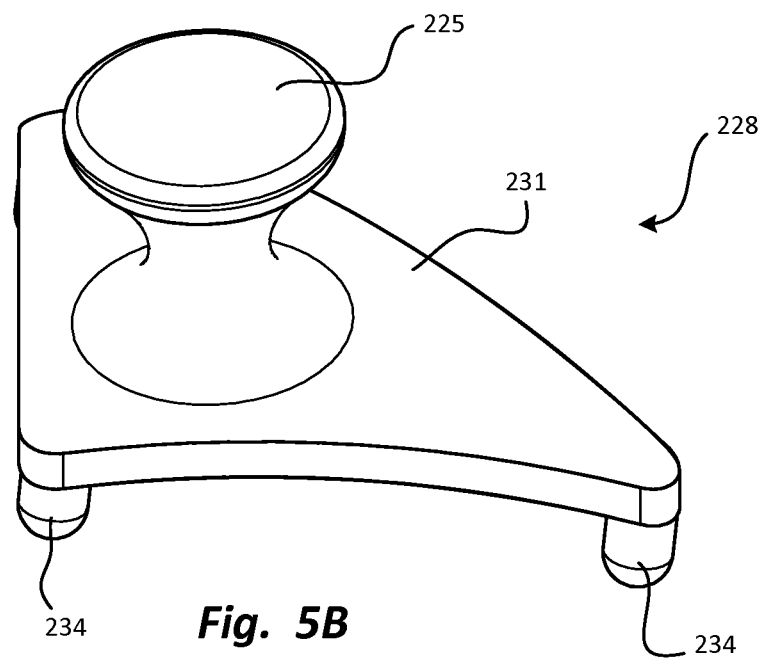

Referring to FIGS. 5A-5B, front elevation and perspective views, respectively, illustrate a template for attaching a plurality of points or markers to the patient to serve as a reference for attachment of a targeting system such as that of FIG. 1 to the patient. As illustrated in FIGS. 5A-5B, the template may include a baseplate 228 with plurality of posts 234 that protrude from the bottom portion 233. These posts 234 may be designed to engage registration markers or fiducials which are commonly used by various image guidance systems. Such fiducials may be held in place on the anatomical feature to which the targeting system (such as the system 10 of FIG. 1) is to be attached by the posts 234. Additionally, the baseplate 228 may include a handle 225 extending form the top portion 231 of the baseplate 228. In some cases, the posts 234 themselves may act as registration markers. In operation, the fiducials (or the posts 234) may be visualized using imaging modalities such as CT scanning or MRI scanning. The posts 234 may be attached to or embedded within the baseplate 228 with a predefined geometry, and may be used in operation to calculate a reference point through the process of registration.

In the event that fiducial markers different from the posts 234 are used, the fiducial markers may be placed onto tissue in a pre-defined geometry using a baseplate 228. These fiducial markers may be incorporated into the baseplate 228 and may thus include elements such as radio-opaque materials, MRI contrast enhancing materials (e.g. copper sulfate), and the like. These fiducial markers may also be external to the baseplate 228 but connected to it. The fiducial markers may be attached to soft tissue such as skin via an adhesive backing or the like, or may be secured directly to bone via screws and/or other fasteners. In general, attachment of the baseplate 228 to the patient may involve any combination of methods to form a solid connection. This includes but is not limited to, adhesives, hook and loop fastener such as Velcro™, and other fasteners including but not limited to clamps, spring-loaded grips, screws, and pins. The manner in which attachment is accomplished may depend on the surgical application, the anatomical location, the type of visualization needed, and the surface properties at the anatomical location (e.g. soft tissue thickness, bone quality, and the like).

In one example of a method of use of a system 10 as in FIGS. 1-3C and a template 228 as in FIGS. 5A-5B, an operator may place fiducial markers at an anatomical region of interest. If attached to the skin, the fiducial markers may be attached to areas of the body with bony prominence and/or minimal soft tissue in order to minimize distortion and shift. Cross-sectional imaging such as CT scanning or MRI scanning may then be performed to visualize these unique markers and generate a reference coordinate system. For example, for cranial navigation, a location with minimal soft tissue may advantageously minimize skin shift; thus, the fiducial markers may be attached to the forehead. For orthopedic applications, the iliac crest and the anterior tibia are examples of anatomical locations with minimal soft tissue coverage.

After imaging has been carried out, the desired trajectory may be established by referring to the image(s) obtained. This trajectory may be used, through the use of known geometrical transformations, to determine the required orientations of the first laser 12 and the second laser 14. The first laser 12 and the second laser 14 may be oriented at the necessary orientations and activated to project the first light 18 and the second light 20, thereby also projecting the targeting line 22. The targeting line 22 may advantageously be projected on a surgical instrument or a visualization aid, as will be shown and described in greater detail subsequently.

The orientations of the first laser 12 and the second laser 14 may be configured automatically and/or manually. If desired, a targeting system may include a mechanism by which the user may read and/or adjust the orientations of the first laser 12 and the second laser 14 manually.

Figure 6A:
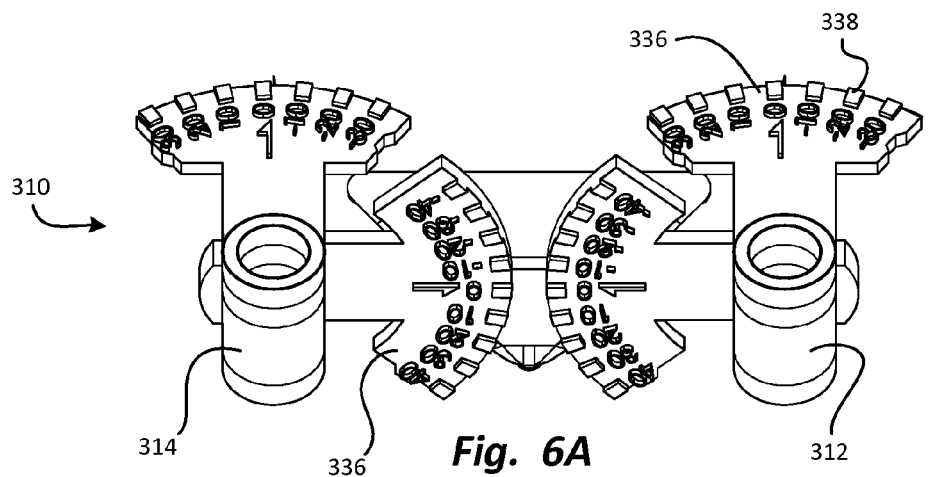
FIGS. 6A-6C are plan, front elevation, and perspective views, respectively, of a targeting system according to another embodiment, with manual adjustment of the laser angles and base posts to mate with a plurality of fiducial markers (references) on the patient.
Figure 6B:
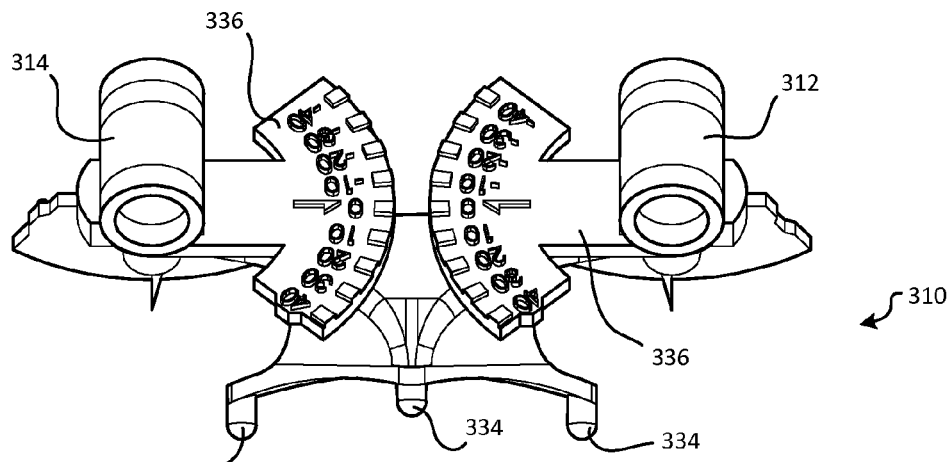
Figure 6C:
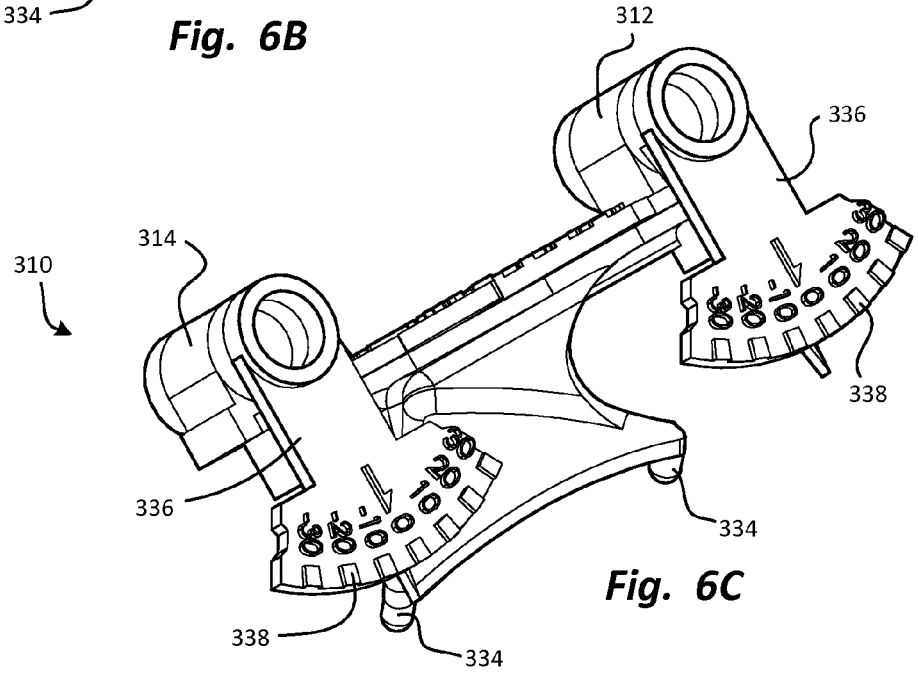
Figure 7A:
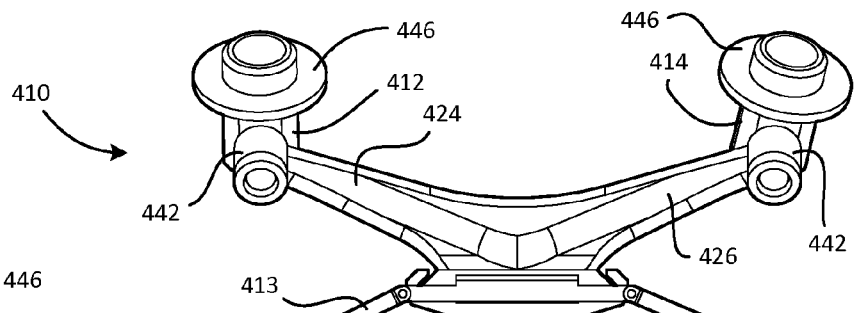
FIGS. 7A-7D are front elevation, perspective, plan, and side elevation views, respectively, of a targeting system according to yet another embodiment, with electronic angle readout and automated (motorized) laser angle adjustment, and a baseplate as in FIG. 3.
Figure 7B:
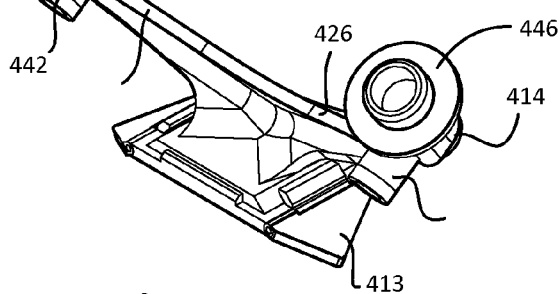
Figure 7C:
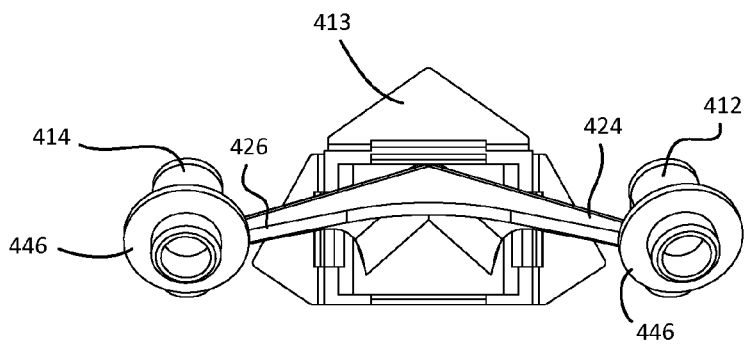
Figure 7D:
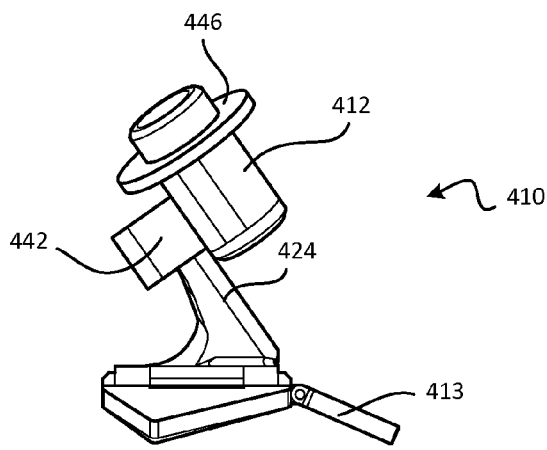

Referring to FIGS. 6A-6C, plan, front elevation, and perspective views, respectively, illustrate a targeting system, or system 310, according to another embodiment. The system 310 may have a first laser 312 and a second laser 314, and may provide for manual adjustment of the orientations of the first laser 312 and the second laser 314. Additionally, the system 310 may have feet that mate with a plurality of fiducial markers (not shown) on the patient. Such fiducial markers may be attached, for example, through the aid of a base plate 228 such as that of FIGS. 5A-5B, as set forth above. The feet may take the form of posts 334, which may register in such fiducial markers or other registration attachments.

In one example, as illustrated in FIGS. 6A-6C, the system 310 may also include angle indicators 336, which may take the form of precision-machined discs. The first laser 312 and the second laser 314 may each be rotatable in the "roll" and "yaw" directions, but not in the "pitch" direction. Thus, the angle indicators 336 may also be referred to as "roll" and "yaw" angle indicators. The angle indicators 336 may have pre-determined radii with markings 338 etched, embedded, or otherwise provided to indicate the magnitude of the angle. The roll angle and/or the yaw angle of each of the first laser 312 and the second laser 314 may be adjusted to the desired number mechanically by rotating the first laser 312 and the second laser 314 around the roll axis and/or the yaw axis. Once a desired angle has been obtained, a locking mechanism such as setscrews or locking screws may be engaged to lock the system 310 into the desired configuration.

Referring to FIGS. 7A-7D, front elevation, perspective, plan, and side elevation views, respectively, illustrate a targeting system, or system 410, according to yet another embodiment. The system 410 may have electronic angle readout and automated (motorized) laser angle adjustment in combination with a first arm 424, second arm 426, and base component 413 like that of FIGS. 3A-3C.

In the system 410 of FIGS. 7A-7D, rotary encoders 442 may be used to couple the a first laser 412 and a second laser 414 to the first arm 424 and the second arm 426, respectively. The rotary encoders 442 may provide digital readouts of the angle measurements (i.e., orientations) of the first laser 412 and the second laser 414. In this example, the first laser 412 and the second laser 414 may be connected to a controller (not shown in FIGS. 7A-7D), which may have a signal processing unit. Such a controller may be a dedicated module, a computer, a smartphone, a tablet, or the like. The controller may provide power to the first laser 412 and the second laser 414 and the rotary encoders 442, and may also receive the orientation output from the rotary encoders 442. In this application, the term "controller" does not require that a device issue operational commands to other components; rather, a controller may be any type of electrical device that interfaces with one or more other components of a targeting system.

Such a controller may additionally or alternatively control the orientation of the first laser 412 and the second laser 414 by transmitting signals to motors that rotate the first laser 412 and the second laser 414 to the desired orientation. In some embodiments, the controller may be connected to a first set of motors that controls the orientation of the first laser 412, and a second set of motors that controls the orientation of the second laser 414. Such motors will be shown and described subsequently, and may include servo motors, stepper motors, and the like. Such motors may be coupled directly to the first laser 412 and the second laser 414, or may be connected to them via gears or other torque-transmitting mechanisms. In the case of motorized lasers, the desired angle may be digitally entered or controlled by a software program (for example, a program or app that runs on the controller), and the motors may drive the rotation of the laser units in the roll, pitch, and yaw directions. Another embodiment integrates a motorized unit into the lenses 16 of the first laser 412 and the second laser 414 to perform micro adjustments directly to the lens 16; this may be done in place of or in addition to roll, pitch, and/or yaw orientation adjustments of the first laser 412 and the second laser 414. In alternative embodiments, a user may manually set the orientations of the first laser 412 and the second laser 414, as described previously.

In yet another example, the system 410 may include a built-in power source such as a battery. The system 410 may also have a wireless communication interface that wirelessly transmits the angle readings from the rotary encoders 446 to a controller or other electronic device in order to display them to the user. Automated control of the orientations of the first laser 412 and the second laser 414 may also be accomplished wirelessly. Any known wireless protocol may be used for communications between the first laser 412 and the second laser 414, and the controller.

Targeting systems according to the present disclosure may be attached to other structures besides those of the patient's anatomy. Any stable structure may provide a suitable anchoring point for a fixture of a targeting system. It may be particularly advantageous to secure a targeting system to a medical imaging device; this may facilitate integration of such targeting systems with medical imaging because the locations of the light sources, relative to the imaging device, may remain constant. This may remove the need for fiducial markers to be used in imaging, even for medical imaging systems with movable components such as C-arm X-ray machines.

Figure 8:
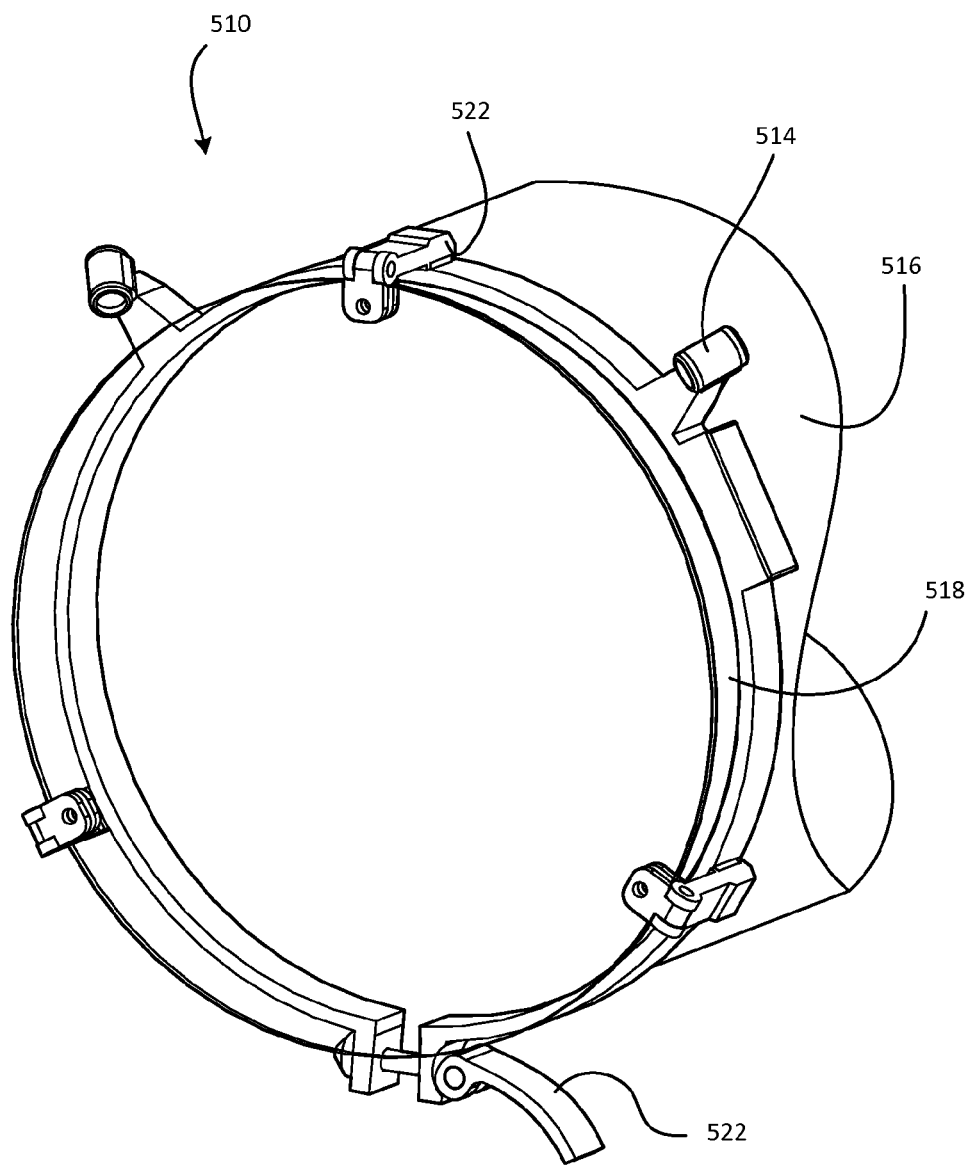
FIG. 8 is a perspective view of a targeting system according to yet another embodiment, for planar imaging modalities with attachment directly to a medical imaging device.

Referring to FIG. 8, a perspective view illustrates a targeting system, or system 510, according to yet another embodiment. The system 510 may be usable for planar imaging modalities with attachment directly to a medical imaging device. For example, the system 510 may be attached to an image intensifier 516 on a fluoroscopy unit. The fluoroscopy unit is used here to facilitate understanding of the concept, and should be understood as a specific embodiment of any general imaging device that takes projections of its subjects from a plurality of angles. The system 510 may readily be adapted for use with other imaging devices such as flat panel charge coupled devices (CCD's).

Figure 9A:
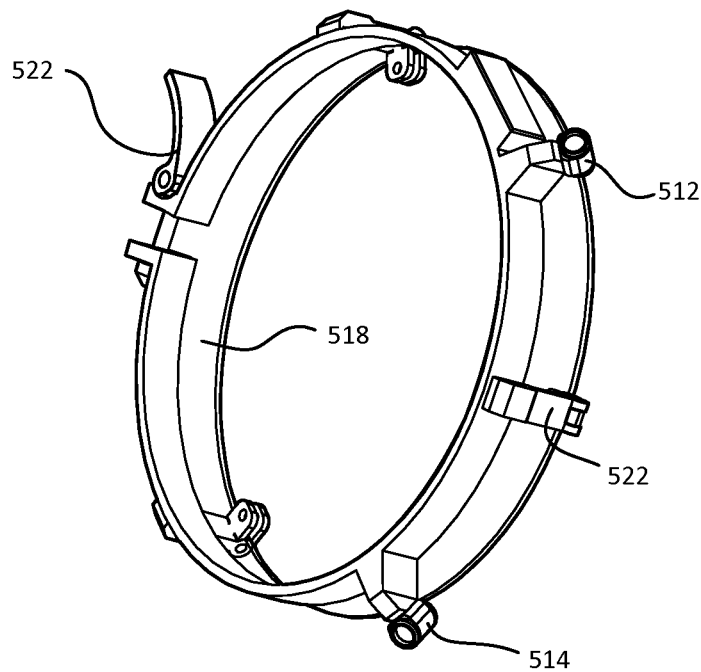
FIGS. 9A-9B are perspective and plan views, respectively, of the targeting system of FIG. 8.
Figure 9B:
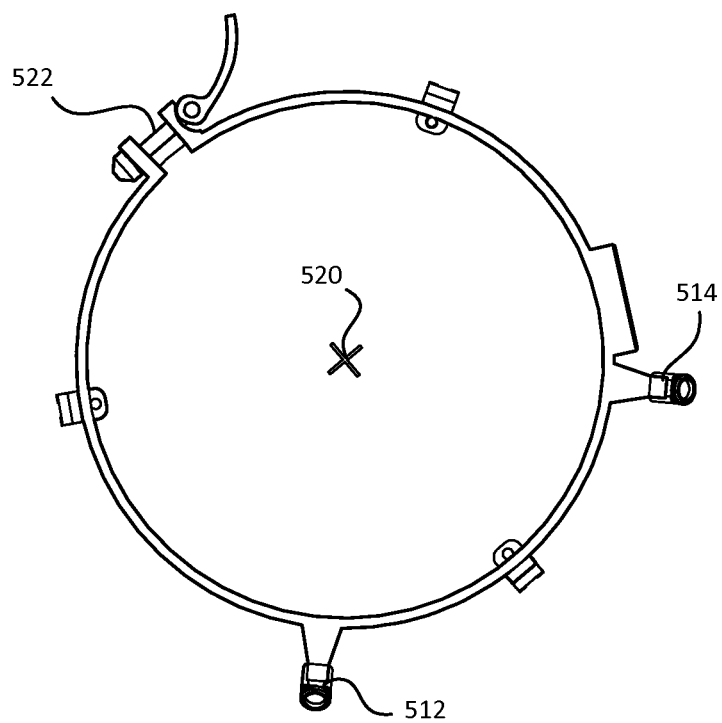

Referring to FIGS. 9A-9B, perspective and plan views, respectively, illustrate the system 510 of FIG. 8. As shown, the system 510 may include a first laser 512 and a second laser 514, both off which may be mounted to the image intensifier 516 via a fixture. In the system 510, the fixture may take the form of a ring 518, which may be concentric with the image intensifier 516 and secured to the image intensifier 516 via locking mechanisms such as screws, snaps, adhesives, or a quick-release mechanism 522. In known medical imaging devices, the image intensifier 516 may be expected to range from 9-11 inches in diameter; however, the image intensifier 516, and therefore the ring 518, may be larger or smaller than this. The ring 518 may extend about the entire circumference of the image intensifier 516, or may be a split ring or other structure that extends only around a portion of the circumference of the image intensifier 516.

The first laser 512 and the second laser 514 may be attached to the ring 518, and the orientations of the first laser 512 and the second laser 514, relative to the ring 518, may be adjustable, manually and/or electronically, as described in connection with the exemplary embodiments of FIGS. 6 and 7. In addition, the distance between first laser 512 and the second laser 514 along the ring 518 may be adjustable, as long as an accurate measurement of such distance can be obtained and accounted for in the angle calculation algorithm.

The system 510 may also include additional light sources, which may be additional lasers. Whether two lasers are used, or more than two, the lasers may be mounted around the image intensifier 516 in such a way that the intersection of the light emitted by the lasers produces the targeting line. The targeting line may be coincident with the central axis of the imaging device, but is not limited by it. The first laser 512 and the second laser 514 may be used to visualize the planned trajectory via projection of the targeting line, and a third laser at oblique angles to the first two may be used to further specify an angle of rotation about the targeting line, a depth of insertion of a surgical instrument along the visualized trajectory, or the like. A third laser may also be used in combination with the first laser 512 or the second laser 514 to produce a second targeting line coplanar with the first targeting line. The second targeting line may be positioned to intersect the first targeting line to specify a single point in three-dimensional space. If a fourth laser is added, then two separate (not necessarily coplanar) targeting lines may be produced simultaneously. The latter example can also be used to specify the angle of rotation around a first targeting line, and depth of insertion along the first targeting line, simultaneously. A marker 520, which may be radio-opaque, may optionally be centered over the image intensifier 516 and secured to the ring 518. This marker 520 may help to identify the center of the image intensifier 516 and should be aligned with the axis of the X-ray tube.

The light sources (for example, the first laser 512 and the second laser 514, returning to the system 510 as illustrated, in which only two light sources are present) may be either fixed in place relative to the image intensifier 516, or movable relative to the image intensifier 516. Fixed lasers, based on the example derived from the system 510, may be placed 90 degrees apart from each other to maximize accuracy. Movable lasers may be more applicable in the setting of a C-arm based CT scanner. These systems rely on the principle of cone-beam CT scanning and swing the C-arm through 180 degrees to obtain an accurate three-dimensional dataset. Some are portable and some are fixed to the room they are installed in. The laser guidance system can be attached to part of the C-arm (e.g. flat panel detector, image intensifier, X-ray tube or the arm itself). The 3-D dataset can be used to plan the trajectory. Based on knowledge of spatial location of the C-arm and the desired trajectory, the orientations of the first laser 512 and the second laser 514 can be calculated to reproduce the desired trajectory in physical space.

Figure 10:
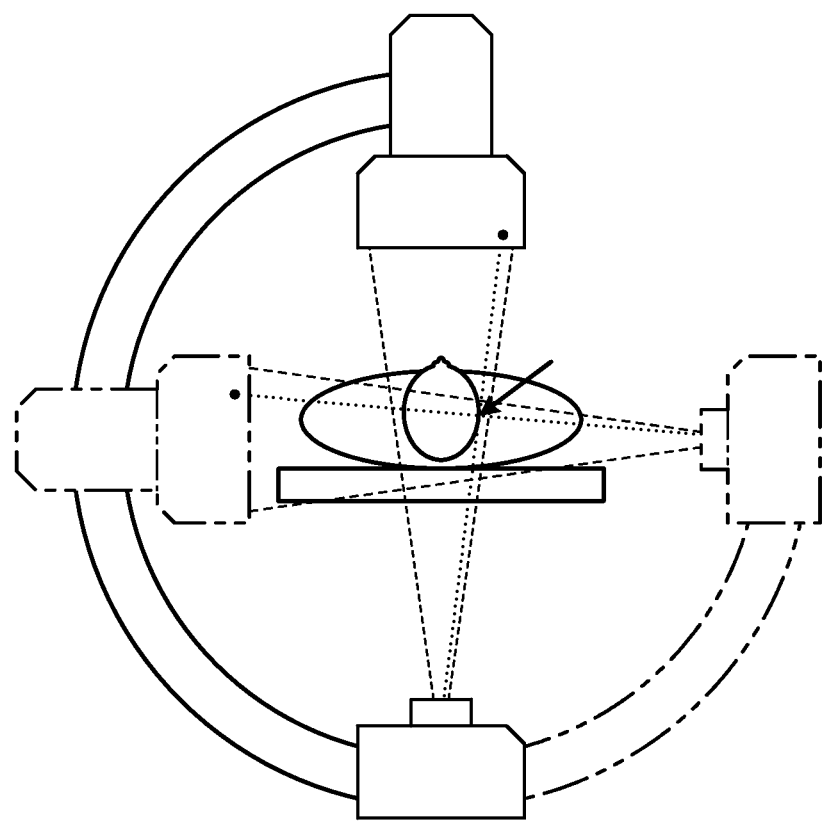
FIG. 10 is a front elevation view of an operating table and patient with a trajectory to be visualized with a targeting system attached to a C-arm fluoroscopy unit, illustrated in two orthogonal imaging positions.

Referring to FIG. 10, a front elevation view illustrates an operating table and patient with a trajectory to be visualized with a targeting system attached to an imaging device in the form of a C-arm fluoroscopy unit, illustrated in two orthogonal imaging positions. As an extension of the embodiment of the laser targeting system in the setting of planar imaging modality, methods for trajectory planning and angle calculation are developed. The imaging device in the form of a C-arm fluoroscopy unit is used for illustration purposes, but the concept can be generalized to any planar imaging modality utilizing penetrating radiation (e.g. monoplane or biplane angiography units). The solid black outline shows the imaging device taking an image at one position. The phantom outline shows the imaging device taking a second image after rotating 90 degrees. The patient is illustrated here in supine position with feet pointed into the page. The cross at the center of the image marks the idealized center of rotation of the imaging device. The two planar image projections are related to each other via this common center of rotation. Thus, during image acquisition, the imaging device is only allowed to undergo pure rotation.

The dashed lines show the extent of radiation field captured by the image intensifier. The intersection of the two cones of radiation (triangles in FIG. 10 due to lack of perspective) marks the space (also referred to as the navigable space) that is used by the targeting system for trajectory planning and angle calculation. The solid black arrow simulates an external pointer with a tip pointing at an idealized entry site, which may represent a trajectory to be visualized. The dotted lines show the back projections of the pointer tip at each C-arm position extending from the radiation source to the image intensifier. The intersection of the two lines marks a unique point in the navigable space. Slight errors in the imaging device (structural deformation, epicyclic center of rotation, vibration etc.) may result in the dotted lines not meeting at a point, in which case a point in the navigable space that is the shortest distance to both of the lines can be used with an error term appended.

In a similar fashion, a second point in the navigable space (for example, another point on the trajectory) can be chosen to fully define the trajectory. The trajectory is defined with respect to the imaging device. Likewise, the orientation calculations for the first laser and the second laser may also be carried out with respect to the imaging device once proper attachment and calibration is performed for the system. No patient reference is needed with planar imaging modality and accuracy should not be affected as long as the patient is not moved between image acquisition and trajectory visualization.

Referring to FIGS. 11A-11B, dorsal and lateral views, respectively, illustrate how orthogonal images can be used for trajectory planning and visualization with a targeting system for a spinal procedure using a planar imaging modality. FIGS. 11A and 11B illustrate the planning of a trajectory of a pedicle screw insertion. Two orthogonal images of the spinal column—dorsal and lateral—are taken and shown on the left and right screens. The black pointer rests at the ideal entry site in this case at the lateral posterior margin of the pedicle. On the lateral projection, the ideal depth is chosen and marked by the black dot. The dashed arrow shows the trajectory on the lateral projection. As an example, the ratio of A:B can be set to 2:1 to prevent anterior breach of the vertebral body. The dot is back projected on the dorsal view as a dotted line.

To fix the target point, the user chooses the ideal target on the dorsal view, which is shown here as the medial edge of the pedicle (the X). This is done to prevent medial breach of the pedicle. With entry and target points defined, the targeting system (such as the system 510 described previously) now has enough information to calculate the orientations of the first laser 512 and the second laser 514 that are needed to project a targeting line indicative of the desired trajectory. The imaging device is locked at a particular angle (0, 90 or any angle in between) and this measurement is provided to the system 510 to finalize the laser orientation calculation.

Referring to FIGS. 12A-12B, lateral and dorsal views, respectively, illustrate how orthogonal images can be used for trajectory planning and visualization with a laser targeting system for an orthopedic procedure using a planar imaging modality. FIGS. 12A-12B illustrate an orthopedic procedure involving distal locking of an intramedullary nail. Two orthogonal images are taken. The image on the left shows an "ideal hole" next to a shifted hole as is often the case due to divergent radiation path from the beam source. The black pointer rests at the center of the ideal hole. The back projection through the hole, from the radiation source to the image intensifier should provide the ideal path for the distal locking screw. This back projection is digitally added to the image on the right and is shown by the dashed line. The dashed line should go through the tip of the black point, and any discrepancy can be added to the error term.

Based on the available information, a trajectory is formed and laser angles can be calculated. However, it is ideal to also obtain the trajectory of the adjacent hole to save procedural time and reduce radiation exposure to patient and house staff. The left image is used again and the center of the shifted hole is selected (e.g. via the centroid method, represented by the X). The back projection is shown on the right image as the dashed arrow. Since the holes should be parallel to each other, the trajectory from the previous hole is used. The intersection of the two trajectories (dashed arrow and dashed line) at the midline of the screw (length-wise) on the right allows for accurate targeting of the second hole. The imaging device is locked at a particular angle (0 degrees, 90 degrees, or any angle in between) and this measurement is provided to the targeting system (for example, the system 510) to finalize the calculation of the orientations of the first laser 512 and the second laser 514.

Figure 13:
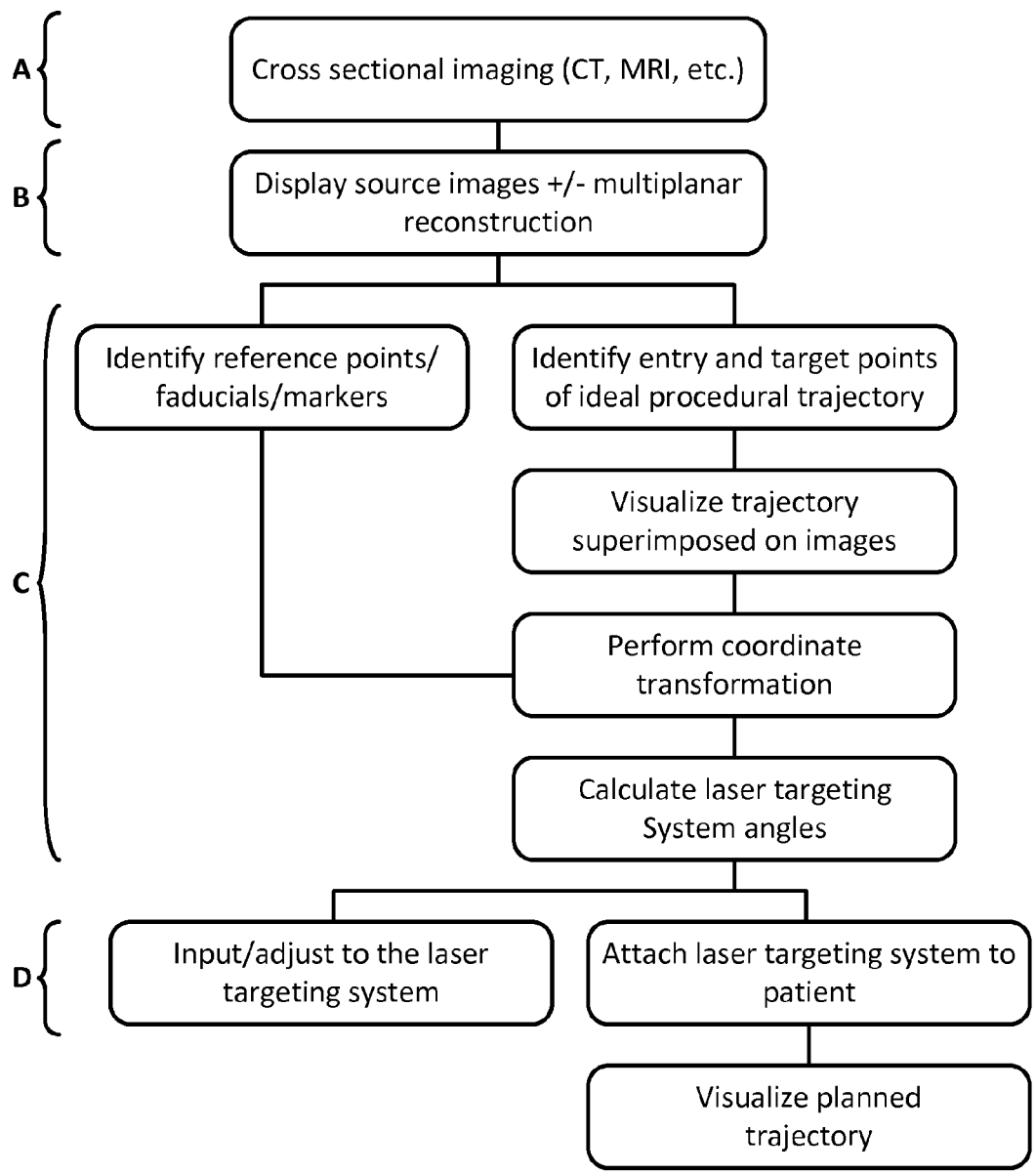
FIG. 13 is a block diagram illustrating one method of using a targeting system in a cross-sectional imaging modality with one or more reference markers attached to the patient.

Referring to FIG. 13, a block diagram illustrates one method of using a targeting system in a cross-sectional imaging modality with one or more reference markers attached to the patient. The method will be described in connection with the system 10 of FIGS. 1-3C, but may be carried out with any targeting system within the scope of the present disclosure. The method may commence with obtaining the image with reference marker(s) attached to the patient (step A).

The sources images as well as any multi-planar reconstructions are then displayed. There are a number of options for this step, including but not limited to: an imaging device terminal such as a CT suite (e.g. CT suite), a diagnostic unit such as a Picture Archiving and Communication System (PACS) unit, or a computer or electronic device (e.g. tablet) capable of displaying Digital Imaging and Communications in Medicine (DICOM) format images (step B).

A software interface is then employed by the user to perform trajectory planning and angle calculations. This can be done either on the same system as step B or on a different system capable of displaying the acquired images. The software interface may be set up to facilitate the flow of image registration (which may also be referred to as reference identification), entry/target point identification, trajectory planning/visualization, and finally laser angle calculation (step C).

One example of the software embodiment of step C may involve the identification of either fiducial markers or baseplate markers such as the posts 234 of FIGS. 5A-5B by the software. The software may then automatically calculate the transformation matrix required to perform a coordinate transformation of the images space onto the laser targeting system's space. The operator may then select the entry point and the target on the cross-sectional image. Multi-planer reconstruction views may be presented to facilitate identification of the most optimal entry/target points. Once the two points are selected, a line in the 3-dimensional image space is constructed which represents the desired trajectory. This line is transformed into the targeting space of the system 10 using the previously derived transformation matrix. Once this is completed, the software may calculate the unique combination of orientations of the first laser 12 and the second laser 14 such that the first light 18 and the second light 20 intersect to produce the targeting line 22 in 3-dimensional space that represents the desired trajectory.

Another example of the software embodiment of step C may involve generation of a trajectory from a set of orthogonal X-ray images. For many orthopedic procedures such as hip/knee arthroplasty or trauma surgery, cross-sectional imaging such as CT scanning is not routinely available. However anterior-posterior (AP) and lateral X-rays are a routine part of the workup for many patients, and intraoperative fluoroscopy is capable to take films in views which are 90 degrees apart. After attaching the reference marker (fiducials or baseplate), two X-rays are taken 90 degrees apart. The end user then identifies the points on both X-rays. Once this is done, a set of x, y, z values is calculated. An additional rotational and scaling transformation is applied to one of the films in order to generate a truly orthogonal coordinate system in the targeting space of the system 10. The ideal trajectory projections are then identified by the end user on the two films, bearing in mind that the trajectory lines identified on the two films are projections of a unique 3-D trajectory onto 2-D space. The backward projections of the two 2-D lines form two planes perpendicular to each of their reference planes and the intersection of these two planes form a unique line in 3-D space, the trajectory. The unique trajectory in 3-D space is then coordinate transformed into the targeting space of the system 10 and calculations of the laser angles are carried out as before.

This method enables the calculation of a trajectory in 3-D space based on projections identified on two 2-D X-rays films orthogonal to each other. It does not specify the projection at any other arbitrary angle of view. For procedures that routinely use plain film X-ray's for follow-up, this is adequate to meet the user's needs since views at other angles are not routinely considered. Step D represents the last step required to visualize the target trajectory.

Figure 14:
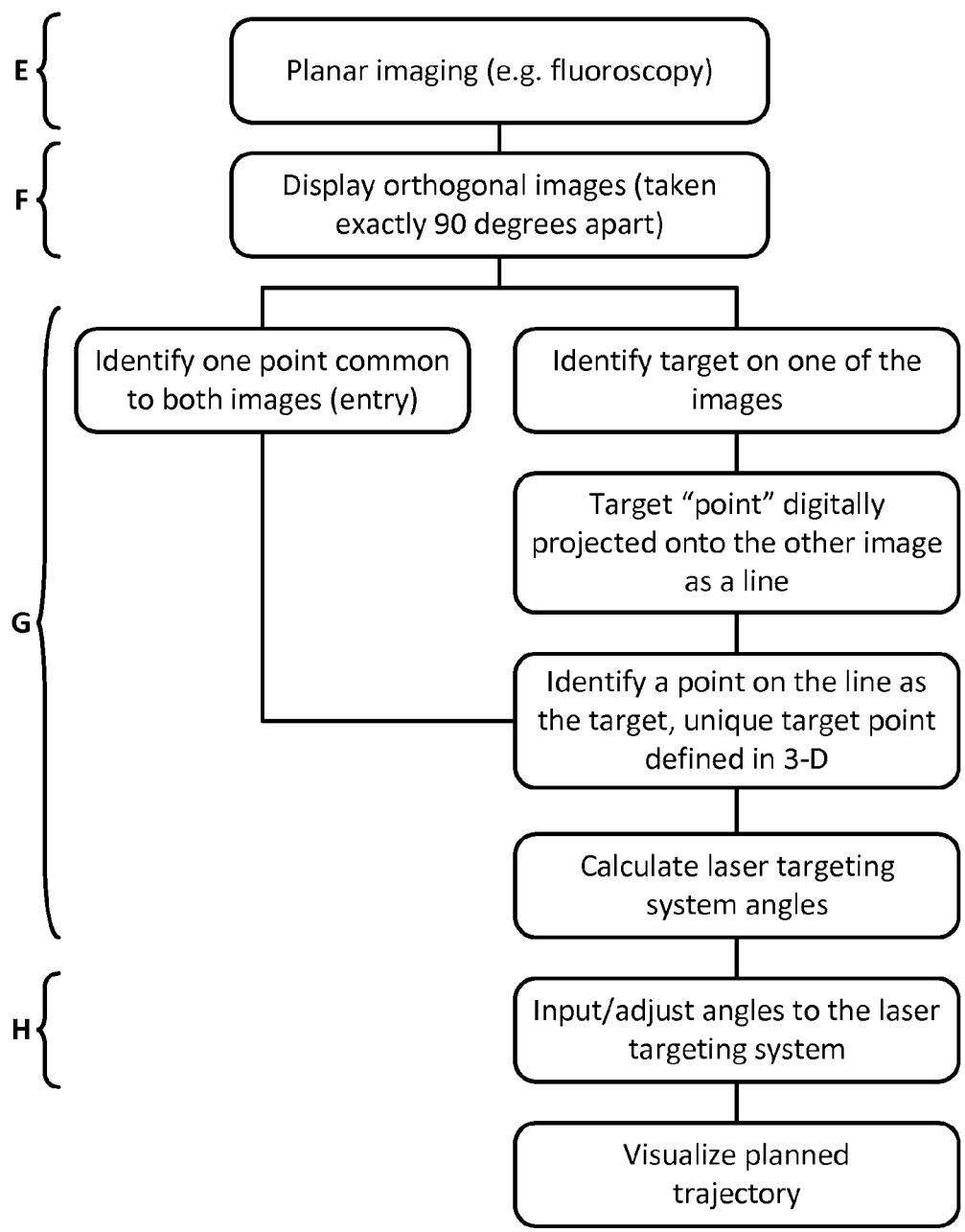
FIG. 14 is a block diagram illustrating one method of using a targeting system in penetrating planar imaging modalities with a minimum of two images taken from orthogonal viewpoints.

Referring to FIG. 14, a block diagram illustrates one method of using a targeting system in penetrating planar imaging modalities with a minimum of two images taken from orthogonal viewpoints. A minimum of two orthogonal images of the anatomical area of interest may first be obtained as described in FIGS. 10-12 (step E).

The images are displayed. Options for display include, but are not limited to: the imaging device terminal (e.g. fluoroscopy screen), a diagnostic unit (e.g. PACS), a computer or electronic device (e.g. tablet) capable of displaying DICOM format images (step F).

A software interface is then required for the user to perform trajectory planning and angle calculations. This can be done either on the same system as step F or on a different system capable of displaying the acquired images. The software interface is setup to facilitate the flow of entry/target point identification, trajectory visualization, and finally laser angle calculation (step G). Examples of step G are provided in FIGS. 11 and 12 in accordance with their respective exemplary embodiments. Step H represents the last step required to visualize the target trajectory for the planar imaging modality.

To help visualize the targeting line(s) and/or the appropriate depth of travel for a surgical instrument, a visualization guide may be used. Such a visualization guide may be used to facilitate viewing of the targeting line and/or guiding of a surgical instrument along the desired trajectory.

Figure 15:
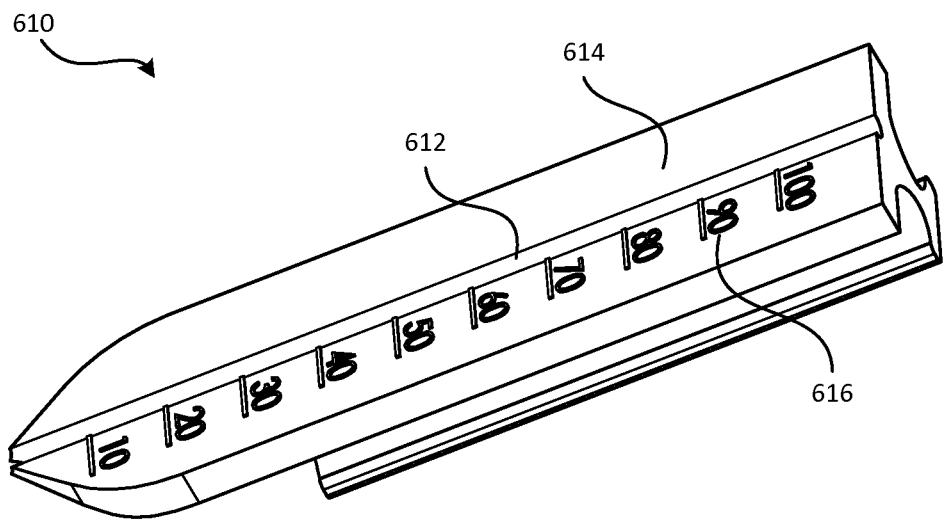
FIG. 15 is a perspective view illustrating a visualization aid in the form of a grooved instrument guide with depth measurement according to one embodiment.

Referring to FIG. 15, a perspective view illustrates a visualization aid 610 in the form of a grooved instrument guide with depth measurement according to one embodiment. The visualization aid 610 will be described in conjunction with the system 10 of FIGS. 1-3C, but may be used with a targeting system according to any embodiment within the scope of this disclosure, including those designed for cross-sectional imaging modalities, and those designed for planar imaging modalities.

The visualization aid 610 may further be a simple open-channel trajectory guide. The visualization aid 610 may thus have a guide surface 612 in the form of an open channel that may be used to conduct a surgical instrument, such as a needle, trocar, cannula, depth probe, implant, or the like, along the desired trajectory. The visualization aid 610 may further have a visualization surface 614 that extends on either side of the guide surface 612 with a widened shape on which the first light 18 and the second light 20, by way of example, may be projected and viewed.

The visualization surface 614 may optionally have a matted or otherwise textured surface that facilitates visualization of reflected light from a wide range of viewing angles. Further, the visualization surface 614 may optionally have depth markings 616 etched, scored, painted, or otherwise marked on the visualization surface 614 to facilitate proper insertion of the surgical instrument. The visualization surface 614 may optionally be white in color to provide for enhanced visibility of reflected light. In alternative embodiments, any color may be used. If the visualization surface 614 is colored, the color of reflected by the visualization surface 614 may not match that of the light emitted by the first laser 12 or the second laser 14. The visualization surface 614 may alternatively be black to reduce glare from light interference; in such an event, the luminance provided by the first laser 12 and the second laser 14 may need to be increased to compensate for the increased light absorption of the black color. The visualization aid 610 may be opaque, translucent, and/or transparent.

For embodiments with an opaque construction, the first light 18 and the second light 20 may reflect off of the visualization surface 614. Thus, the first light 18 may be visible on the visualization surface 614 as a first line, and the second light 20 may be visible on the visualization surface 614 as a second line with a color different from that of the first line. If the first and second lines are nonparallel, this may indicate that the visualization aid 610 needs to be reoriented. If the first and second lines are parallel, but displaced from each other, this may indicate that the visualization aid 610 needs to be translated toward or away from the first laser 12 and/or the second laser 14. As the first and second lines converge (i.e., the linear displacement and/or angular displacement between the first and second lines is reduced as needed), the targeting line 22 may be visible on the visualization surface 614 and/or the guide surface 612. Due to the additive properties of light, the targeting line 22 may have a color different form that of the first line and different from that of the second line. Thus, the convergence of the first and second lines and/or the appearance of the targeting line in the additive color may indicate that the visualization aid 610 is reaching the position and orientation of the desired trajectory.

For embodiments with a transparent or translucent construction, the first light 18 and the second light 20 may penetrate the body of the visualization aid 610 and, when the visualization aid 610 is aligned with the desired trajectory, cause the visualization aid 610 to glow in the additive color to confirm proper alignment of the visualization aid 610 with the desired trajectory.

Thus, the visualization aid 610 may improve the visualization of the first light 18, the second light 20, and the targeting line 22, thereby easing the process of aligning a surgical instrument with the desired trajectory. Additionally, the guide surface 612 may help to guide the insertion of devices. The depth markings 616 may allow the visualization of depth information during insertion process. The visualization aid 610 may additionally or alternatively include features such as an enclosed tube, rail, channel, or other mechanical fitting that interacts with implants and/or surgical instruments to align those implants and/or surgical instruments with the desired trajectory.

In processes in which sterility is not of a critical importance, a device capable of atomizing water droplets, suspending particulates in the air, or forming fogs or fog-like states can be used. Such procedures may enable direct visualization of the targeting line 22 in the suspended particulates or vapor without the need for a flat surface to reflect the light.

To further aid the visualization process, one or more fiber optic features can be incorporated into the guide surface 612. The light from the targeting line 22 may be directed down the fiber optic tract to further aid visualization. Additional electronic components can also be incorporated into the trajectory guide to analyze the light intensity and colors. For example, a photo diode or charged couple device (a rectangular grid or line-type CCD) or CMOS sensor can be used to monitor the incoming light. The signal output can be connected to the electronic component described above and used to provide feedback to the user regarding accuracy of trajectory alignment. Furthermore, in alternative embodiments, the visualization aid 610 may be incorporated into other medical devices, such as the body of an ultrasound probe or surgical instrumentation set (e.g. drill, screwdriver, rod holder etc.) to provide directly visualization of the trajectory.

Figure 16:
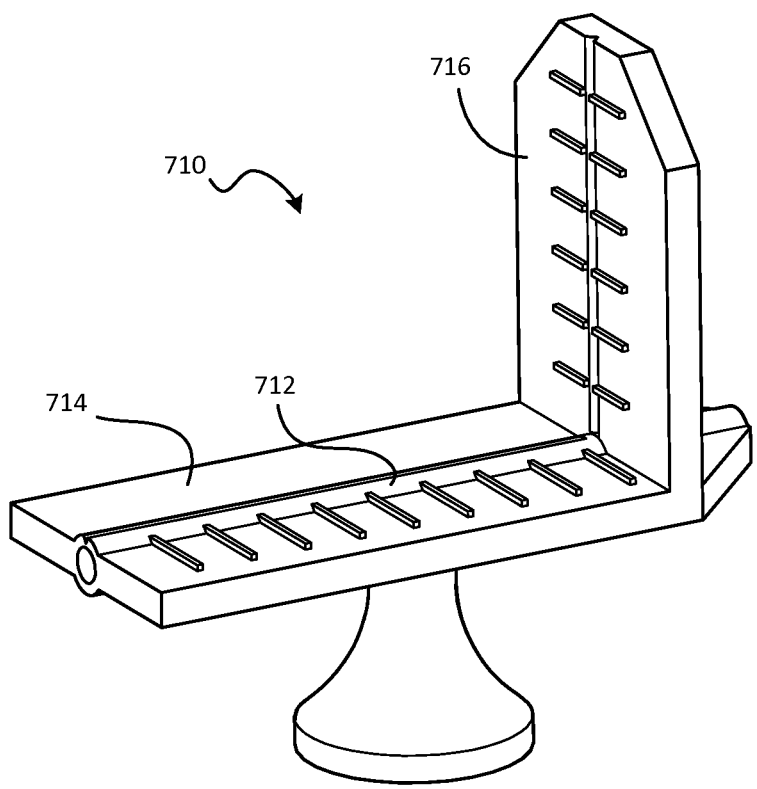
FIG. 16 is a perspective view illustrating another visualization aid in the form of an enclosed channel and depth control, which may help to visualize the primary targeting line as well as a secondary targeting line projected from one or two additional light sources of the targeting system.

Referring to FIG. 16, a perspective view illustrates another visualization aid 710 in the form of an enclosed channel and depth control, which may help to visualize the primary targeting line as well as a secondary targeting line projected from one or two additional light sources of the targeting system. As shown, the visualization aid 710 may take the form of a trajectory guide with a guide surface in the form of the bore of an enclosed tube 712 with a visualization surface 714 on either side of it. Further, the visualization aid 710 may have an orthogonal alignment piece 716 that may be used for visualization of a secondary targeting line or other feature projected by one or more additional light sources (for example, a third and/or fourth laser).

The visualization surface 714 may function in a manner similar to that of the visualization surface 614 of the visualization aid 610 of the previous embodiment. The enclosed tube 712 may be used to guide surgical instruments such as catheters, needles, drills, and the like. The orthogonal alignment piece 716 may be perpendicular to the tube 712 and may provide visualization of a third and/or fourth light source.

For example, a third laser that projects light nonparallel to the first light 18 and nonparallel to the second light 20 can be used. The intersection of this third laser with the targeting line can be visualized on the orthogonal alignment piece 716. This alignment may define the degree of rotation along the desired trajectory, thereby fixing another degree of freedom. The amount of rotation along the planned trajectory can be planned on the cross-sectional or planar imaging, and the third light source can be moved accordingly after the appropriate calculations are performed.

If a fourth laser is added, then the intersection of the third and fourth lasers will form a second targeting line. The orientations of the light sources can be calculated such that this second targeting line intersects with and is orthogonal to the first (primary) targeting line formed by the first laser 12 and the second laser 14. This may not only lock in rotation, but may also provide depth visualization. This adds control of another degree of freedom in the depth direction along the desired trajectory.

Figure 17:
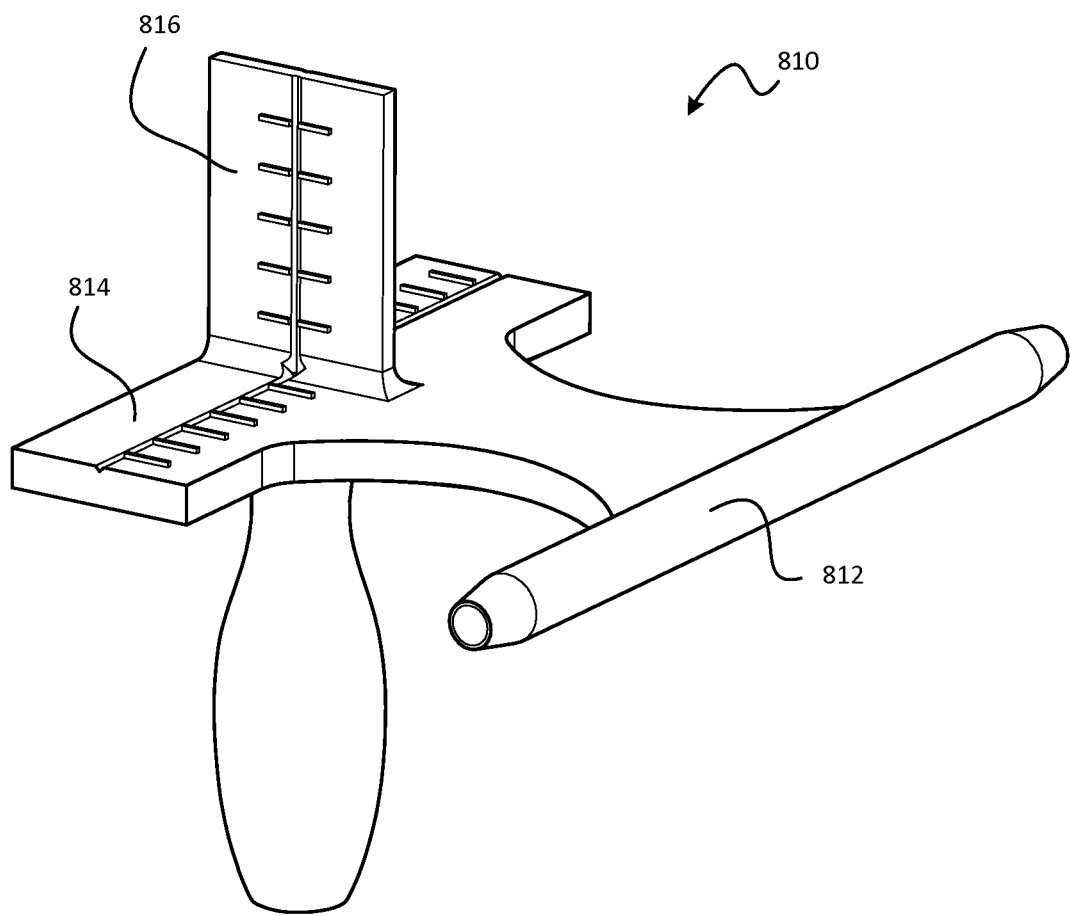
FIG. 17 is a perspective view illustrating another visualization aid in the form of an offset enclosed channel and depth control, which may help to visualize the primary targeting line as well as a secondary targeting line projected from one or two additional light sources of the targeting system, while providing an actual trajectory offset from the targeting line(s).

Referring to FIG. 17, a perspective view illustrates another visualization aid 810 in the form of an offset enclosed channel and depth control. The visualization aid 810 may facilitate visualization of the primary targeting line as well as a secondary targeting line projected from one or two additional light sources of the targeting system, while providing an actual trajectory offset from the targeting line(s).

The visualization aid 810 may have a guide surface in the form of the bore of an enclosed channel 812. In alternative embodiments, the visualization aid 810 may instead have a guide surface with an open channel, a series of rings, and/or or any number of features that allow the visualization aid 810 to be used to guide instruments and/or implants. The visualization aid 810 is similar to that of FIG. 16 in that the targeting line 22 may be visualized in addition to a secondary targeting line or other features that provide visualization of orientation and/or depth control, depending on the number of light sources used in the targeting system. The visualization aid 810 may thus have a visualization surface 814 and an orthogonal alignment piece 816, which may function in a manner similar to their counterparts of FIG. 16.

The visualization aid 810 may position the enclosed channel 812 at any desired distance and/or orientation with respect to the visualization surface 814 and the orthogonal alignment piece 816, as long as this orientation is known beforehand and factored into the calculations. In alternative embodiments, the angular and/or linear displacement between the guide surface and the visualization surface may be made adjustable, so long as the relative positioning of the visualization and guide surfaces can be accurately measured and accounted for in the calculations. If any adjustment to the relative orientation and/or position of the guide surface and the visualization surface occurs after performance of the calculations, a new set of measurements may need to be taken and calculations may need to be performed again.

Any of the visualization aids disclosed herein may be made to attach to the patient or a targeted object in a wide variety of ways. Various attachment mechanisms may be employed, depending on the surface properties of the attachment site, including adhesives, hook and loop fasteners such as Velcro™, pins, screws, clamps, jaws, etc.

Alternatively or additionally, a separate stand and/or support arm may be provided to hold the visualization aid in place. This may be a standalone unit with its own stand and adjustable arm to aid positioning and/or keep the visualization aid in place. Alternatively or additionally, such an adjustable support arm can be made attachable to an operating room table, an imaging device (e.g. a C-arm), or any suitable feature on the targeted object.

Such a support arm can be further motorized and integrated with a robotic control system to provide a semi-automated or fully-automated alignment process. Such systems can be connected to the controller mentioned above to allow communication with the user. Additionally or alternatively, such a support arm can be incorporated into a robot-assisted procedure as outline above.

The visualization aid may be further adjustable with respect to the attachment base/arm system. A locking mechanism may be provided, and may have a set screw, thumb screw, clips, quick release mechanism, and/or other mechanism that provides releasable locking to secure the visualization aid in the desired configuration once the appropriate alignment is obtained. This may free the hand(s) of the operator from holding the visualization aid securely at all times to allow him or her to focus on the procedure itself.

Figure 18:
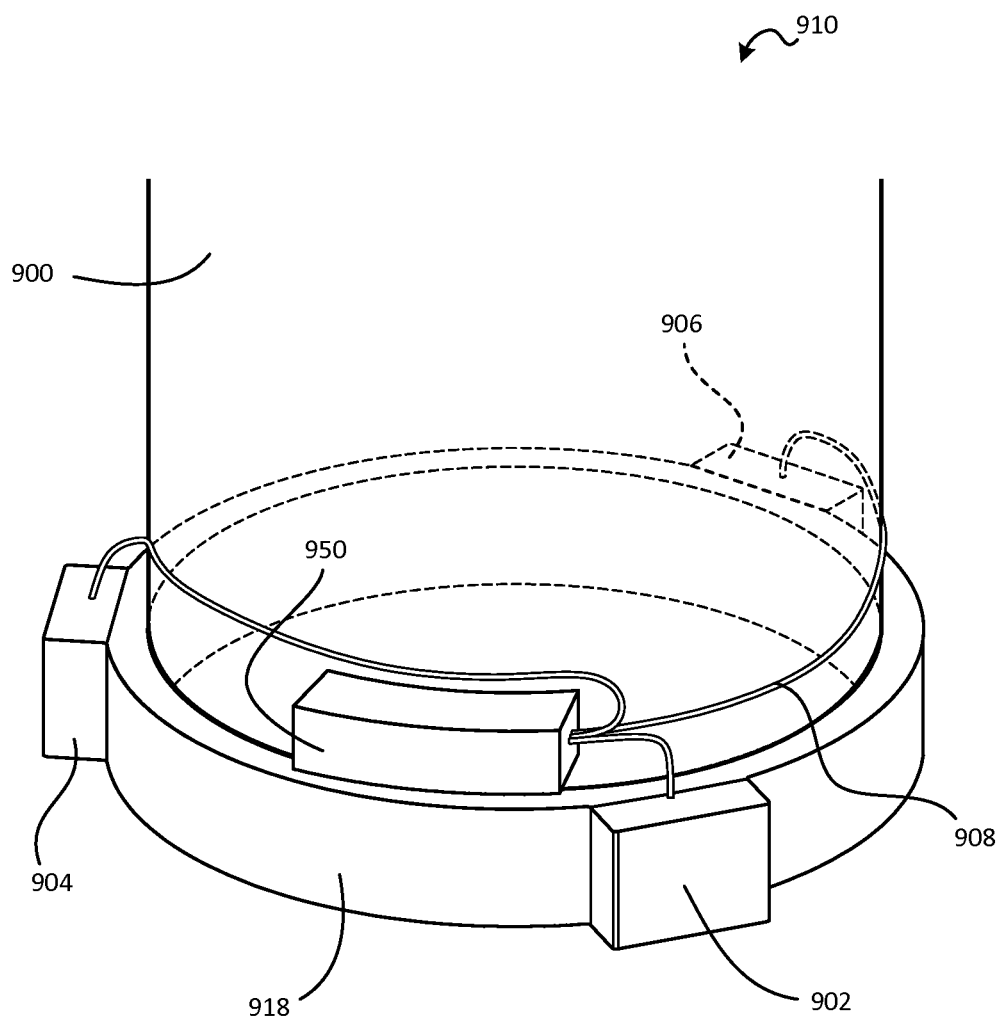
FIG. 18 is a perspective view illustrating a targeting system according to another alternative embodiment of the invention.

Referring to FIG. 18, a perspective view illustrates a targeting system, or system 910, according to another alternative embodiment of the invention. Like the system 510 of FIGS. 8-9B, the system 910 may be designed for attachment to a medical imaging device, such as the imaging intensifier 900 of a C-arm fluoroscopy unit. The system 910 may include a first light source in the form of a first light module 902, a second light source in the form of a second light module 904, and a third light source in the form of a third light module 906. The system 910 may also include a fixture in the form of a ring 918, and a controller 950.

The first light module 902, the second light module 904, and the third light module 906 may each be fixedly secured to the ring 918. The first light module 902 may contain a first light source (not shown) such as a first laser, and may also contain a first set of motors (not shown) capable of changing the orientation of the first laser. Similarly, the second light module 904 may contain a second laser (not shown) and a second set of motors capable of changing the orientation of the second laser. Further, the third light module 906 may contain a third laser (not shown) and a third set of motors capable of changing the orientation of the third laser. Hence, although the first light module 902, the second light module 904, and the third light module 906 may be substantially rigidly attached to the ring 918, the corresponding light sources may be oriented at the necessary orientations to provide visualization of a desired trajectory.

As shown, the controller 950 may be electrically coupled to the first light module 902, the second light module 904, and the third light module 906 via wires 908. The controller 950 may receive data from the first light module 902, the second light module 904, and the third light module 906, such as the actual orientations of the first, second, and third lasers. Additionally or alternatively, the controller may transmit signals to the first light module 902, the second light module 904, and the third light module 906 to activate the first, second, and third lasers and/or set the orientations of the first, second, and third lasers.

As mentioned previously, the use of more than two light sources allows additional visualization to shown, such as the desired orientation and/or depth of a surgical instrument at the desired trajectory. Alternatively, the use of more than two light sources allows the optimal two light sources to be used; thus, in the event that a light source is blocked or is not optimally positioned to provide accurate visualization of the desired trajectory, other light sources may be used instead. Positioning the first light module 902, the second light module 904, and the third light module 906 at an even distribution about the periphery of the image intensifier 900 may enhance the likelihood that at least two light sources of the system 910 will be unobstructed and positioned for accurate projection of the targeting line. In other embodiments, more than three light sources may be used.

Figure 19:
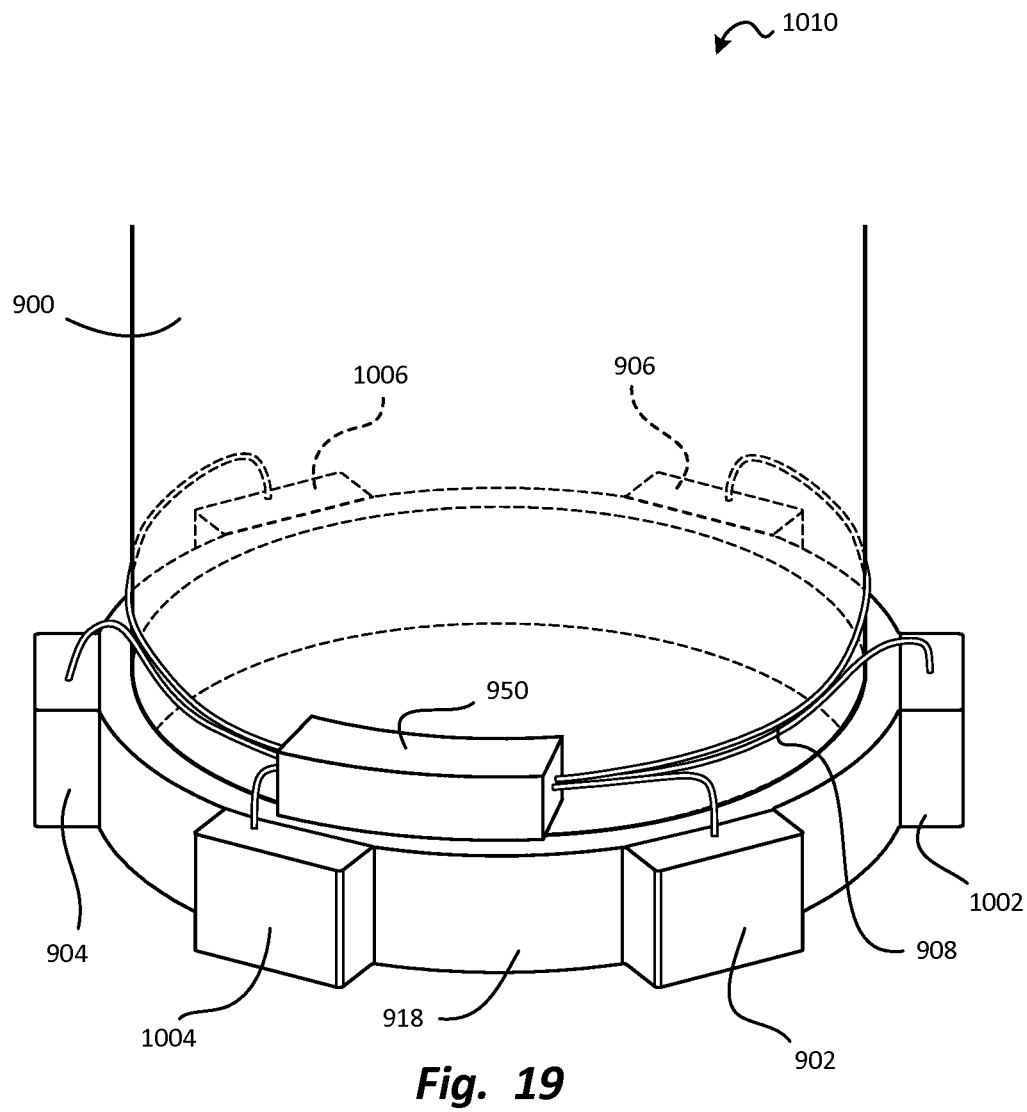
FIG. 19 is a perspective view illustrating a targeting system according to yet another alternative embodiment of the invention.

Referring to FIG. 19, a perspective view illustrates a targeting system, or system 1010, according to another alternative embodiment of the invention. The system 1010 may have a configuration similar to that of the system 910, except that the system 1010 may have additional light sources. More specifically, in addition to the first light module 902, the second light module 904, and the third light module 906, the system 1010 may have a fourth light module 1002, a fifth light module 1004, and a sixth light module 1006. These may be fixedly attached to the ring 918, but may contain fourth, fifth, and sixth light sources, which may be fourth, fifth, and sixth lasers that are movable relative to the ring 918.

The use of six light sources may enable the projection of additional features and/or lines. Further, the use of six light sources may further enhance the likelihood that at least two light sources of the system 1010 will be unobstructed and positioned for accurate projection of the targeting line.

Figure 20:
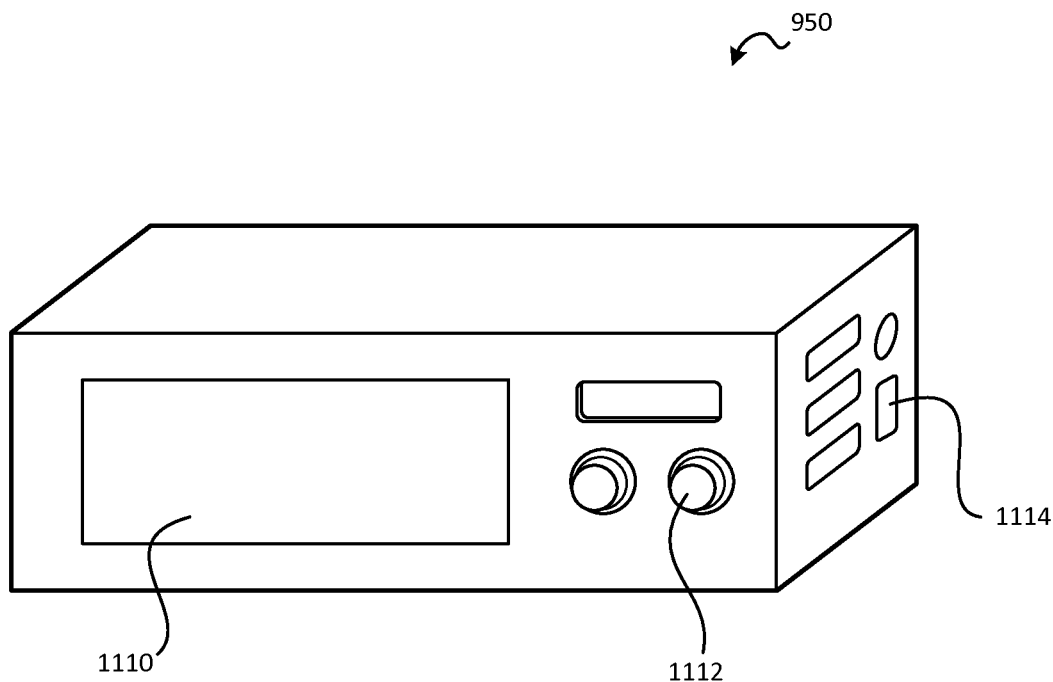
FIG. 20 is a perspective view of the controller of FIGS. 18 and 19.

Referring to FIG. 20, a perspective view illustrates the controller 950 of FIGS. 18 and 19 in greater detail. As shown, the controller 950 may have a display 1110, a control interface 1112, and connection ports 1114. The display 1110 may, for example, display the angulation of any or all of the light modules connected to it. Such data may come from the light modules. Additionally or alternatively, the controller 950 may have a built-in gyroscope or other measurement device that indicates the angle at which the controller 950 is positioned. When used on a mobile platform such as a movable medical imaging device, the mobile platform may be moved back to a datum position (for example, the first position at which imaging data was captured) in order to provide a meaningful indication of orientation.

The control interface 1112 may be used by the user to change the settings of the system 910 or the system 1010, manually key in the orientations of the light sources, turn light modules on or off, manually enter the position and/or orientation of the desired trajectory, or the like. The connection ports 1114 may be used to connect the controller 950 to other components such as the light modules, the medical imaging device to which it is attached, an external computer, or the like. If desired, the controller 950 may receive orientation data for the light modules and/or the desired trajectory directly from the medical imaging device or an external computer. Thus, the controller 950 may be designed to operate independently of any direct user input.

Figure 21A:
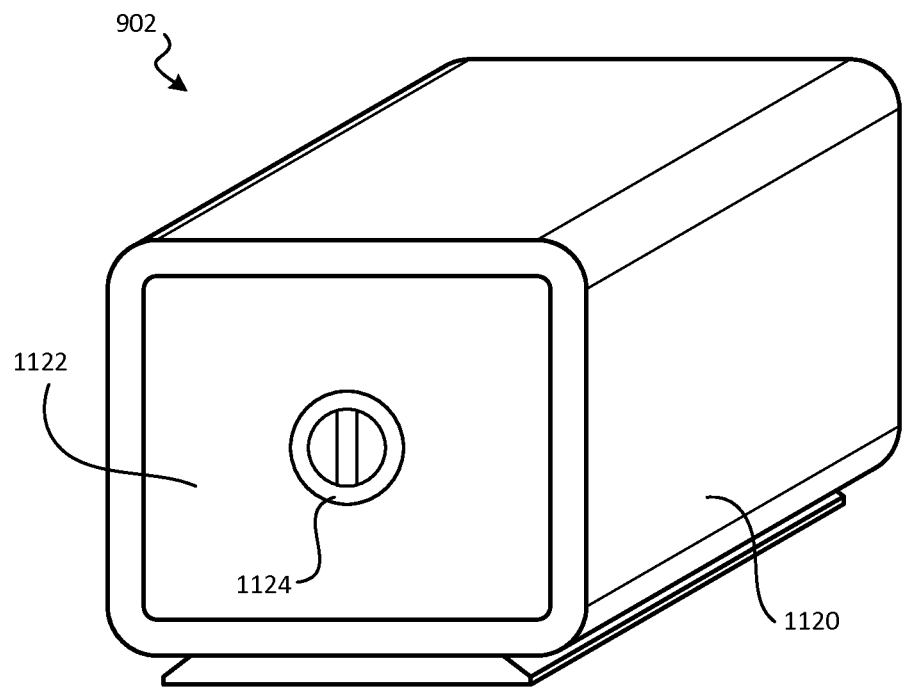
FIGS. 21A and 21B are perspective and front elevation views, respectively, of the first light module of FIGS. 18 and 19.
Figure 21B:
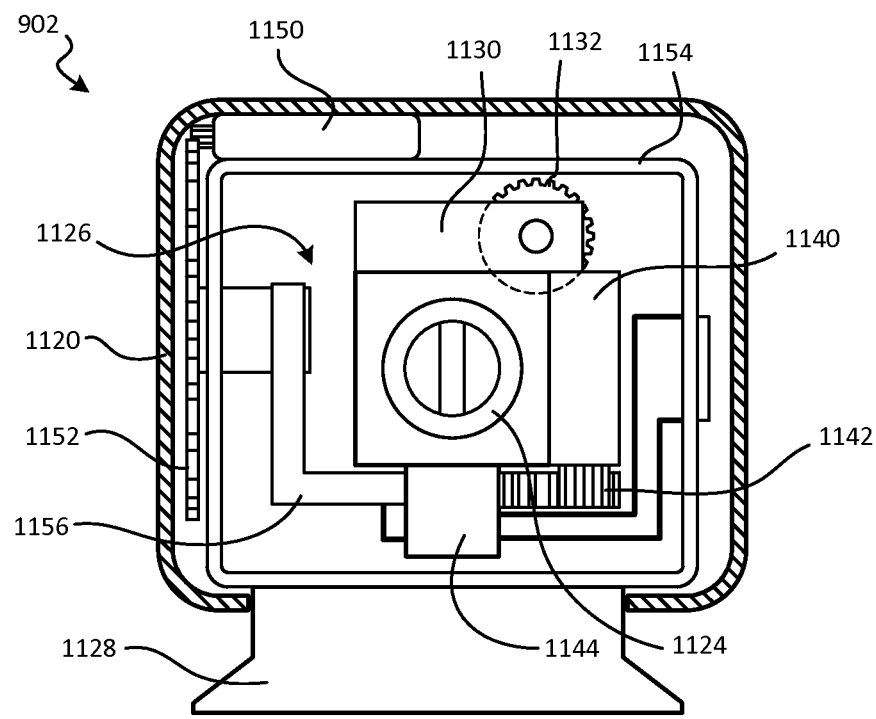

Referring to FIGS. 21A and 21B, perspective and front elevation views, respectively, illustrate the first light module 902 of FIGS. 18 and 19 in greater detail. The first light module 902 may be substantially the same as the other light modules, i.e., the second light module 904, the third light module 906, the fourth light module 1002, the fifth light module 1004, and the sixth light module 1006.

The first light module 902 may have a housing 1120 with the overall shape of a rectangular prism. The housing 1120 may be formed of a polymer if desired, for the purpose of limiting the weight of the targeting system. The housing 1120 may be hollow, and may contain a first light source, which may be a first laser 1126 as mentioned previously. The first laser 1126 may have a slotted cap 1124 that causes the light emitted by the first laser 1126 to propagate along a plane, i.e., the first plane as discussed in connection with FIG. 1.

The first light module 902 may also have a window 1122 that is translucent to permit light from the first laser 1126 to exit the housing 1120. If desired, the window 1122 may be tinted to act as a filter. Thus, the window 1122 may, if desired, be used to determine the wavelength(s) of light that form the first light emitted by the first light module 902. The window 1122 may only permit light of a certain wavelength range to exit the housing 1120. Alternatively, the first laser 1126 may be designed to emit light of the desired color. In such a case, the window 1122 may be untinted, and need not act as a filter.

As shown in FIG. 21B, the first light module 902 may also have an attachment interface 1128 designed to facilitate removable, yet secure attachment of the first light module 902 to the ring 918. The attachment interface 1128 may take the form of a dovetail base that mates with a corresponding undercut slot (not shown) formed in the ring 918. In alternative embodiments, other fastening systems may be incorporated into an attachment interface, including but not limited to screw-mounted systems, slidable quick-release systems, and the like.

The first light module 902 may have a first set of motors that controls the orientation of the first laser 1126 within the housing 1120. For example, the first set of motors may include a roll control motor 1130, a yaw control motor 1140, and a pitch control motor 1150. The roll control motor 1130 may adjust the "roll" orientation of the first laser 1126, the yaw control motor 1140 may adjust the "yaw" orientation of the first laser 1126, and the pitch control motor 1150 may adjust the "pitch" orientation of the first laser 1126.

The pitch control motor 1150 may be positioned adjacent to an internal frame 1154 within the housing 1120. The internal frame 1154 may contain a swivel bracket 1156 that is pivotably connected to the internal frame 1154 such that the swivel bracket 1156 can rotate within the internal frame 1154 to permit adjustment of the pitch of the first laser 1126. The pitch control motor 1150 may be coupled to the swivel bracket 1156 via pitch control gearing 1152, so that rotation of an output shaft of the pitch control motor 1150 causes the swivel bracket 1156 to angle the first laser 1126 upward or downward, relative to the view of FIG. 21B.

The yaw control motor 1140 may be positioned on the swivel bracket 1156, adjacent to the first laser 1126. The first laser 1126 may be pivotably coupled to the swivel bracket 1156 via a transverse shaft 1144. The transverse shaft 1144 may rotate to permit the first laser 1126 to rotate leftward or rightward, relative to the view of FIG. 21B. The yaw control motor 1140 may be coupled to the transverse shaft 1144 and/or the adjacent portion of the swivel bracket 1156 via yaw control gearing 1142. Rotation of an output shaft of the pitch control motor 1150 may cause the first laser 1126 to rotate relative to the swivel bracket 1156.

The roll control motor 1130 may be positioned above the first laser 1126. The roll control motor 1130 may be coupled to the first laser 1126, or to just the slotted cap 1124, via roll control gearing 1132. Thus, rotation of an output shaft of the roll control motor 1130 may cause the first laser 1126 and/or the slotted cap 1124 to roll about an axis perpendicular to the page, with respect to the view of FIG. 21B.

As mentioned previously, a light source need only have an adjustable orientation about two orthogonal axes. However, providing orientation adjustment about all three axes may provide for additional flexibility in the operation of the targeting system. If desired, any one of the roll control motor 1130, the yaw control motor 1140, and the pitch control motor 1150 may be omitted, if desired, to immobilize the first laser 1126 as applied to rotation about the corresponding axis.

Figure 22A:
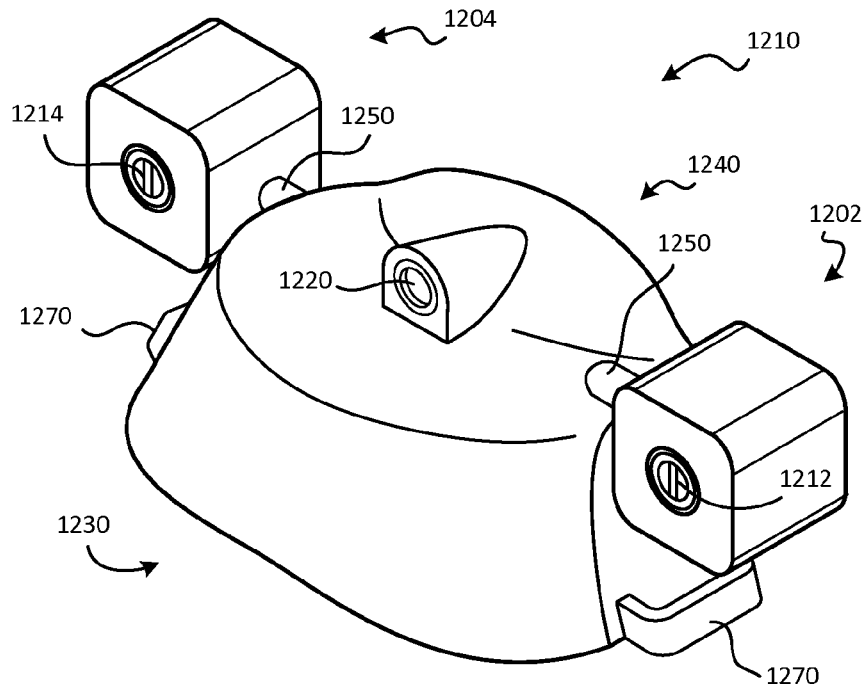
FIGS. 22A and 22B are perspective and front elevation section views, respectively, of yet another alternative embodiment of the invention with integration of an image-capture device.
Figure 22B:
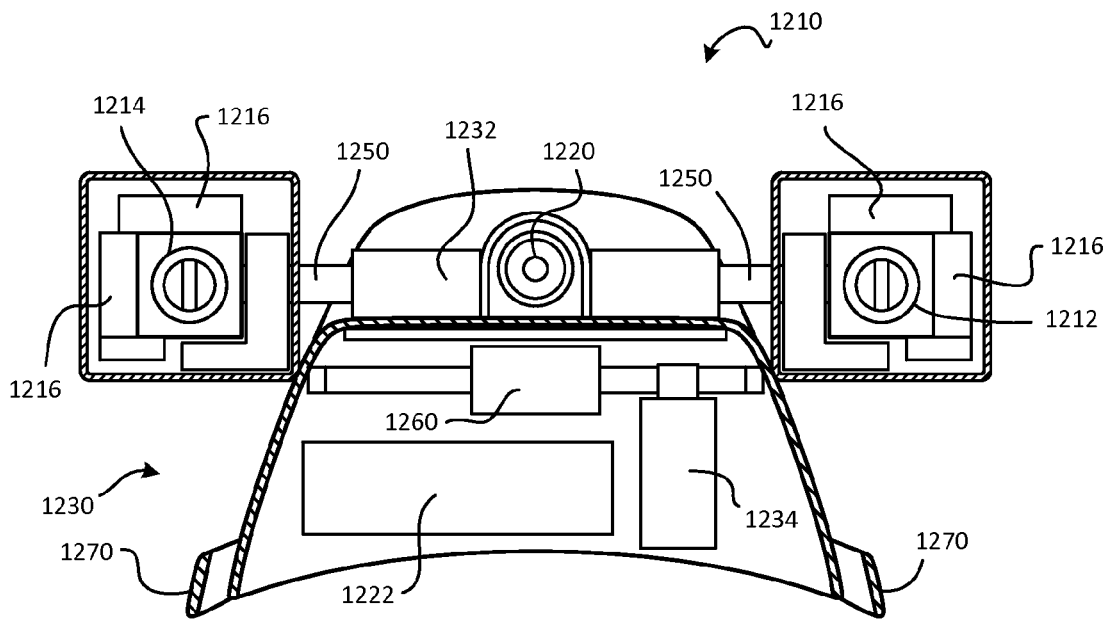

Referring to FIGS. 22A and 22B, perspective and front elevation, section views, respectively, illustrate a targeting system, or system 1210, according to another alternative embodiment of the invention. An image-capture device may be integrated into the system 1210. The image capture device may take the form of a camera 1220 mounted to the body of the system 1210. The camera 1220 may include various imaging technologies, including but not limited to CCD (charge coupled display) sensors, CMOS (complementary metal-oxide-semiconductor) sensors, and the like. Digital output from the camera 1220 may facilitate the operation of the system 1210, but in alternative embodiments, analog and/or film-based cameras may be used. For procedures that require a targeting system to be mounted on the patient, the system 1210 depicted in FIGS. 22A and 22B represents a fiducial-free method of obtaining accurate registration.

Additionally, the system 1210 may have a fixture in the form of a base unit 1230, an armature 1240, and laser mounting posts 1250 on the armature 1240, on which a first laser module 1202 and a second laser module 1204 are mounted. The camera 1220 may be on the armature 1240, which may be movable relative to the base unit 1230. The first laser module 1202 may have a first laser 1212 that is rotatable within the first laser module 1202 about at least two of the roll, pitch, and yaw axes described previously. Similarly, the second laser module 1204 may have a second laser 1214 that is rotatable within the second laser module 1204 about at least two of the roll, pitch, and yaw axes. Motion of the first laser 1212 and the second laser 1214 within the first laser module 1202 and the second laser module 1204 may be accomplished through the use of motors 1216, as shown in FIG. 22B.

The base unit 1230 may be securable to an external structure adjacent to the patient, including but not limited to armature, pole, platform, and the like. The base unit 1230 may also be securable to a portion of the patient's anatomy. Where the system 1210 is to be used for a cranial procedure, such as installation of an EVD, as discussed previously, the base unit 1230 may be secured to cranial anatomy, such as the forehead. For other procedures, the system 1210 may be attached to a different location on the patient. As mentioned before, locations with relatively little soft tissue covering the underlying bone may provide optimal locations for registration. This may facilitate the use of attachment features in the form of non-invasive attachment mechanisms 1270 to attach the system 1210 to the patient, such as straps, grips, adhesives, and/or the like. Additionally or alternatively, if desired, the system 1210 may be secured through soft tissue to underlying bone through the use of screws or other devices.

The camera 1220 is positioned at a known distance from the first laser module 1202 and the second laser module 1204. The first laser module 1202 and the second laser module 1204 may project first light and second light (not shown) along first and second planes (not shown), respectively to provide a targeting line. When projected onto a surface, such as a portion of the patient's anatomy, the first light, the second light, and/or the targeting line may reflect off of the surface. The reflection, including any attendant distortion, may be captured by the camera 1220. Through triangulation, given the known positions of the first and second planes relative to the camera 1220, the system 1210 may determine the coordinates, in three-dimensional space, of the anatomical features intersecting the first light and the second light. Thus, at a given angle between the first laser 1212 and the camera, the triangulation process produces a line of information in 3D space. By slowly scanning the laser line across an object and capturing images at each angle increment, a full three-dimensional dataset can be built-up that accurately represents a 3D surface.

In FIG. 22A, the first light module 902 is directly connected to a controller 1222. The system 1210 may use the first laser module 1202 and the second laser module 1204 to scan across the patient's anatomical region of interest. The laser light may be rotated about a single axis at set degree intervals (for example, yaw at 5 degree intervals) and the camera 1220 may capture an image at each such interval. The controller 1222 may generate a three-dimensional map of the surface of the patient's anatomical region. This may be done, for example, by comparing the reflection of the first light, the second light, and/or the resulting targeting line to a pre-defined set of reference images saved in a database. This three-dimensional surface may then be matched to the three-dimensional surface generated from patient imaging. Patient imaging in this instance may include any set of 3D images such as one or more CT scans or MRI scans. The trajectory planned using such imaging may be used in conjunction with the three-dimensional surface information to calculate the pitch, yaw and/or roll orientations of the first laser 1212 and the second laser 1214. The first laser module 1202 and the second laser module 1204 may be set at the proper orientations and activated to produce a targeting line at the desired trajectory without the need of any fiducials attached to the patient.

One laser module (i.e., either the first laser module 1202 or the second laser module 1204) is sufficient to capture the necessary 3D surface data from the patient. Both the first laser module 1202 and the second laser module 1204 may be used to improve the accuracy of the system and reduce "blind spots." When the first laser module 1202 and the second laser module 1204 are both used, the first laser 1212 may be scanned across the patient's anatomical region, followed by the second laser 1214. The images are captured and processed, and the distortions of the reflections of the first light and the second light from the patient's anatomy are matched to the respective databases of the first and second laser lines. The resulting cloud-point data are added to generate the final 3D surface map.

In FIG. 22B, the controller 1222 may be connected to one or more motors that move the armature 1240 relative to the base unit 1230. The motors may include, for example, a pitch motor 1232 that controls the pitch of the armature 1240 relative to the base unit 1230, and a yaw motor 1234 that controls the yaw of the armature 1240 relative to the base unit 1230. The armature 1240 may be rotatably coupled to the base unit 1230 via a bearing 1260. The pitch motor 1232 may, if desired, cause the laser mounting posts 1250 to rotate relative to the armature 1240. The first laser module 1202, the second laser module 1204, and the camera 1220 may be secured to the laser mounting posts 1250 such that rotation of the laser mounting posts 1250 causes the pitch of the first laser module 1202, the second laser module 1204, and the camera 1220 to change. The system 1210 may cause the pitch and/or yaw of the camera 1220, the first laser module 1202, and/or the second laser module 1204 to change to position the camera 1220 at the most optimal vantage point relative to the anatomical region of interest. This may improve the quality of the 3D surface map and thence, improve the accuracy of registration of the system 1210 on the relevant anatomy and projection of the targeting line.

The system 1210 may also use image subtraction to further increase contrast of the laser line scan. The camera 1220 may first take an image of the anatomical area of interest without the first laser 1212 and/or the second laser 1214 turned on, thereby acquiring a baseline image. The first laser 1212 and/or the second laser 1214 may then be activated, and image acquisition may proceed at set degree intervals as described above. The baseline image may be subtracted from the acquired set of images to effectively eliminate background pixels, leaving only the reflected light from the first laser 1212 and/or the second laser 1214. To maximize registration accuracy, the patient's anatomical area of interest should have distinctive 3D features. Since the facial area has many such distinctive features, the system 1210 is well adapted to cranial applications.

General characteristics of a targeting system according to the present disclosure may include light weight, since the image guidance system may rest upon a patient's skin. The light sources may be made from lightweight materials, such as polymers, composites, lightweight metal alloys, or the like. Electronics miniaturization is contemplated; on-board electronics may be surface-mount with small footprints. Lightweight rechargeable batteries may be used, such as lithium-polymer or lithium-ion batteries.

The disclosed technology is versatile and has a wide range of applications. The aforementioned examples are for illustration purposes to facilitate understanding of concepts; they do not imply that the targeting systems and methods disclosed herein are restricted to only those procedures. Other applications include but are not limited to other medical applications whereby the system may be utilized to target anatomical structures. This includes procedures such as biopsy of tissues where an entry and target can be specified and the trajectory is planned to avoid critical neurovascular structures. Further, this includes ablations or electrical stimulation procedures to target an area that cannot be directly visualized (e.g. rhizotomies, neuromodulation procedures).

Further, the targeting systems and methods of the present disclosure may be applied to joint injections such as knee/hip/shoulder or facet joint injections. The targeting systems disclosed herein may be adapted for guidance or alignment of implants. For example, alignment of a hip prosthesis can be performed either with pre-operative cross-sectional imaging such as CT scanning or planar imaging taken intra-operatively using fluoroscopy. The system can provide trajectory information for alignment of an acetabular cap and femoral shaft, for example. Similarly, alignment of a knee replacement can be performed whereby the system guides the osteotomy cuts on the tibial or the femoral ends. Appropriate planning can be carried out on cross-sectional imaging pre-operatively or intra-operatively on the fluoroscopy images. Other joint replacement procedures that can benefit from trajectory visualization include ankle, elbow, or shoulder replacements. Artificial intervertebral discs can be aligned using the targeting system to maintain anterior-posterior orientation, lateral orientation, and/or true midline position. For spinal fusion procedures, the targeting system can be used to align implants such as contact cages, bone grafts, anterior cervical plates, lateral spinal plates, pedicle screws, pars screws, facet screws, and the like.

The targeting systems and methods disclosed herein can also be used guide other instruments. Examples include catheter placement procedures, whereby a rigid or semi-rigid catheter is directed at an anatomical target. Again, planning can be carried out on cross-sectional or planar imaging to a defined entry, target, and a safe trajectory.

An external ventricular drain (EVD) for neurosurgical patients is an example of a catheter placement procedure that may benefit from trajectory visualization and planning to avoid injury to critical structures. Port planning for rigid endoscopes is another example of trajectory visualization of surgical instruments. The view through a rigid endoscope can be quite different depending on the placement of the endoscope port and the angle of the shaft. For hip or knee scopes, the ideal view can be planned ahead of time on either cross-sectional or planar imaging. The endoscope trajectory can then be calculated and the entry port marked precisely.

The targeting systems and methods disclosed herein can also be used with ultrasound probes to integrate multiple imaging modalities. This allows the user to take advantage of the most optimal tissue visualization for a given procedure. For example, initial planning can be carried out via bony landmarks on X-ray or CT scan. Once a trajectory is defined, the soft tissue along that trajectory can be further visualized using an ultrasound probe with the probe's central axis directly along the planned trajectory.

The targeting systems and methods disclosed herein can also be used with existing image guidance systems. The laser modules and controller may be mounted in various ways including but not limited to: on the camera of image guidance systems, externally on fixed support structures, directly on the patient, and the like. The controller may interface with image guidance systems. Software integration may allow the image processing terminal (for optical based systems, this is usually the workstation connected to the camera) to be used for planning trajectory and laser position calculation. The data may then be output to the control unit to steer the light sources to their final positions. In this configuration, the targeting system may augment the functionality of existing image guidance systems while ensuring the surgeon has "eyes on patient" at all times.

Furthermore, the targeting systems and methods disclosed herein can be used with a variety of robot-assisted procedures. This may help the surgeon or surgical team visualize the planned trajectory, especially where a particular step must be performed manually. The manual step can be carried out using the targeting system in addition to the robotic arm's positioning to improve accuracy and speed.

Alternatively, a targeting system as described herein may be mounted on the end of a robotic arm. The robotic arm can be used to position the targeting system in the most optimal position. The rotation of the lasers (for example, roll and yaw) may allow additional degrees of freedom to position the robotic arm such that it will not get in the way of the user while maintaining trajectory visualization accuracy. An example includes robot-assisted hip replacement where by a trajectory line can be projected before a specific step is carried out (e.g. reaming of the acetabulum). The surgeon can visually confirm the trajectory without the robotic arm blocking the view. The reamer can then be attached to the robotic arm or the surgeon can carry out the ream process manually with direct visualization of the ideal trajectory. Again, robot-assisted hip replacement is used here to illustrate the concept, but can be generalized to any robotic assisted procedures or processes.

The targeting systems and methods disclosed herein can also be used for non-medical applications to provide trajectory visualization. Examples include dental applications such as alignment of implant posts. Pre-operatively taken panoramic X-rays or focused CT scans can be performed and planning may be carried out based on the images obtained from the X-rays or CT scans. Once the trajectories are planned, the targeting system, mounted on an X-ray arm or on the patient, can be used to visualize the trajectories. Other dental procedures include defining root canal trajectories and finding dental fractures.

The targeting systems and methods disclosed herein can be further expanded to industrial applications where certain manufacturing processes cannot be fully automated. In situations where an operator is required to perform a task and where trajectory alignment is critical, the targeting system can be used to provide trajectory visualization. The targeting system can be used with manual procedures such as drilling, welding, finishing and fastening, to align the tool with a predefined trajectory to improve the quality of the finished product.

The claims are not to be interpreted as including means-plus- or step-plus-function limitations, unless such a limitation is explicitly recited in a given claim using the phrase (s) "means for" or "step for," respectively. The term "coupled" is defined as connected, although not necessarily directly, and not necessarily mechanically. The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several examples for the purpose of streamlining the disclosure. This method of disclosure is not to be interpreted as reflecting an intention that the invention require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. §112 Para. 6. It will be apparent to those having skill in the art that changes may be made to the details of the above-described embodiments without departing from the underlying principles of the invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

What is claimed is:

1. A targeting system for providing visualization of a trajectory for a medical instrument, the targeting system comprising:
   a fixture comprising a first attachment feature that secures the fixture at a predetermined location relative to a patient;

a first laser attached to the fixture, wherein the first laser projects first light along a first plane centered at a principle axis; and a second laser attached to the fixture, wherein the second laser projects second light along a second plane nonparallel to the first plane such that, at an intersection of the first plane with the second plane, the first light and the second light cooperate to produce a first targeting line that indicates the trajectory;

wherein the first targeting line is nonparallel to the principle axis;

wherein the first light comprises a first wavelength corresponding to a first color within the visible portion of the electromagnetic spectrum;

wherein the second light comprises a second wavelength corresponding to a second color within the visible portion of the electromagnetic spectrum;

wherein the second wavelength is different from the first wavelength and the second color is different from the first color;

wherein the first laser is adjustably attached to the fixture such that adjustment of at least one of a first roll setting, a first pitch setting, and a first yaw setting of the first laser is adjustable to adjust a first orientation of the first plane, relative to the fixture; and wherein the second laser is adjustably attached to the fixture such that adjustment of at least one of a second roll setting, a second pitch setting, and a second yaw setting of the second laser is adjustable to adjust a second orientation of the second plane, relative to the fixture.

2. The targeting system of claim 1, further comprising:
a camera secured to the fixture at a known position relative to the first light source, wherein the camera comprises a central axis nonparallel to the principle axis and captures image data indicating reflections of the first light from anatomical features of a patient; and
a controller that receives the image data to generate a three-dimensional map of the anatomical features and, based on the three-dimensional map, determines, relative to the fixture, a first orientation of the first light source and a second orientation of the second light source at which the first targeting line indicates the trajectory.

3. The targeting system of claim 1, wherein the first attachment feature comprises a first foot shaped to rest on a first location on the patient, wherein the fixture further comprises:
a second foot shaped to rest on a second location on the patient; and
a third foot shaped to rest on a third location on the patient.

4. The targeting system of claim 3, wherein the medical instrument is configured to be inserted into the patient along the trajectory, wherein the fixture is configured such that the first foot, the second foot, and the third foot are spaced apart in a manner that facilitates placement of the first foot at the first location, placement of the second foot at the second location, and placement of the third foot at the third location.

5. The targeting system of claim 1, wherein the fixture is shaped to be secured to a movable imaging component of a medical imaging device, wherein the first light source and the second light source are positioned at different positions on the fixture.

6. The targeting system of claim 1, wherein at least two of the first roll setting, a first pitch setting, and the first yaw setting are adjustable and at least two of the second roll setting, a second pitch setting, and the second yaw setting are adjustable.

7. The targeting system of claim 6, wherein the first laser is incorporated into a first light module comprising the first laser and a first set of motors that are operable to move the first laser to adjust at least two of the first roll setting, the first pitch setting, and the first yaw setting;
wherein the second laser is incorporated into a second light module comprising the second laser and a second set of motors that are operable to move the second laser to adjust at least two of the second roll setting, the second pitch setting, and the second yaw setting.

8. The targeting system of claim 7, further comprising a controller connected to the first set of motors and the second set of motors, wherein the controller receives the trajectory and, based on the trajectory, transmits first signals to the first set of motors to control at least two of the first roll setting, the first pitch setting, and the first yaw setting, and transmits second signals to the second set of motors to control at least two of the second roll setting, the second pitch setting, and the second yaw setting.

9. The targeting system of claim 8, further comprising a medical imaging device that captures at least one image of the patient, receives the trajectory, and transmits the trajectory to the controller.

10. The targeting system of claim 1, further comprising:
a third light source attached to the fixture, wherein the third light source projects third light along a third plane nonparallel to the first plane and the second plane such that any two of the first light source, the second light source, and the third light source are operable to produce the first targeting line.

11. The targeting system of claim 1, further comprising:
a third light source attached to the fixture, wherein the third light source projects third light along a third plane; and
a fourth light source attached to the fixture, wherein the fourth light source projects fourth light along a fourth plane nonparallel to the third plane such that, at an intersection of the third plane with the fourth plane, the third light and the fourth light cooperate to produce a second targeting line simultaneously with production of the first targeting line.

12. The targeting system of claim 1, further comprising a visualization aid comprising:
a visualization surface on which the first targeting line is projected; and
a guide surface positioned such that, with the first targeting line projected on the visualization surface, the medical instrument is slidable along the guide surface to move along the trajectory.

13. A method for providing visualization of a trajectory for a medical instrument, the method comprising:
orienting a first laser at a first orientation by changing at least one of roll, pitch, and yaw of the first laser relative to a fixture to which the first laser is adjustably attached;
orienting a second laser at a second orientation by changing at least one of roll, pitch, and yaw of the second laser relative to the fixture, to which the second laser is adjustably attached;
with the first laser, projecting first light, comprising a first wavelength corresponding to a first color within the visible portion of the electromagnetic spectrum, along a first plane centered at a principle axis;

with the second laser, projecting second light, comprising a second wavelength corresponding to a second color within the visible portion of the electromagnetic spectrum, along a second plane; and at an intersection of the first plane with the second plane, producing a targeting line, nonparallel to the principle axis, that indicates the trajectory relative to a patient;

wherein the second wavelength is different from the first wavelength and the second color is different from the first color.

14. The method of claim 13, further comprising, prior to orienting the first light source and prior to orienting the second light source:

capturing at least one image of a patient; and based on the at least one image, establishing the trajectory.

15. The method of claim 14, wherein the first light source is incorporated into a first light module comprising the first light source and a first set of motors that are operable to orient the first light source, wherein the second light source is incorporated into a second light module comprising the second light source and a second set of motors that are operable to orient the second light source, the method further comprising:

transmitting the trajectory to a controller connected to the first set of motors and the second set of motors;

in the controller, determining the first orientation and the second orientation based on the trajectory; and with the controller, transmitting first signals to the first set of motors to initiate orientation of the first light source at the first orientation; and with the controller, transmitting second signals to the second set of motors to initiate orientation of the second light source at the second orientation.

16. The method of claim 13, further comprising:

positioning a visualization aid;

wherein projecting the first light comprises projecting a first line on a visualization surface of the visualization aid;

wherein projecting the second light comprises projecting a second line on a visualization surface of the visualization aid;

wherein producing the targeting line comprises orienting the visualization aid to a guiding orientation during projection of the first light and during projection of the second light such that the first line and the second line converge to define the targeting line.

17. The method of claim 16, further comprising, with the visualization aid oriented at the guiding orientation, inserting the medical instrument along the trajectory by sliding the medical instrument along a guiding surface of the visualization aid.

18. A targeting system for providing visualization of a trajectory for a medical instrument, the targeting system comprising:

a fixture comprising a first attachment feature that secures the fixture at a predetermined location relative to a patient;

a first light module attached to the fixture, the first light module comprising:

a first light source that projects first light along a first plane; and a first set of motors that are operable to move the first light source to adjust at least two of a first roll setting, a first pitch setting, and a first yaw setting of the first light source;

a second light module attached to the fixture, the second light module comprising:

a second light source that projects second light along a second plane; and a second set of motors that are operable to move the second light source to adjust at least two of a second roll setting, a second pitch setting, and a second yaw setting of the second light source;

a controller connected to the first set of motors and the second set of motors, wherein the controller receives the trajectory and, based on the trajectory, transmits first signals to the first set of motors to control at least two of the first roll setting, the first pitch setting, and the first yaw setting, and transmits second signals to the second set of motors to control at least two of the second roll setting, the second pitch setting, and the second yaw setting; and a visualization aid comprising:

a visualization surface on which a targeting line is projected at an intersection of the first plane with the second plane in response to orientation of the visualization aid at a guiding orientation; and a guide surface positioned such that, with the targeting line projected on the visualization surface, the medical instrument is slidable along the guide surface to move along the trajectory.

* * * * *